United States Patent
Mohler et al.

(10) Patent No.: US 7,273,609 B2
(45) Date of Patent: *Sep. 25, 2007

(54) METHODS FOR TREATING AUTOIMMUNE AND CHRONIC INFLAMMATORY CONDITIONS USING ANTAGONISTS OF CD30 OR CD30L

(75) Inventors: Kendall M. Mohler, Poulsbo, WA (US); Dauphine S. Barone, Mill Creek, WA (US); Mary K. Kennedy, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/506,645

(22) Filed: Aug. 18, 2006

(65) Prior Publication Data

US 2006/0280741 A1  Dec. 14, 2006

Related U.S. Application Data

(62) Division of application No. 10/648,136, filed on Aug. 26, 2003, now Pat. No. 7,122,183, which is a division of application No. 09/921,667, filed on Aug. 3, 2001, now Pat. No. 6,652,854.

(60) Provisional application No. 60/224,079, filed on Aug. 8, 2000.

(51) Int. Cl.
   *A61K 39/395* (2006.01)
   *C07K 21/08* (2006.01)
   *C07K 16/22* (2006.01)

(52) U.S. Cl. .............. 424/133.1; 424/154.1; 424/173.1; 530/387.3; 530/388.23

(58) Field of Classification Search ............. 424/133.1, 424/154.1, 173.1; 530/357.3, 388.23
   See application file for complete search history.

(56) References Cited

U.S. PATENT DOCUMENTS

| | | | |
|---|---|---|---|
| 5,304,635 A | 4/1994 | Imam et al. | |
| 5,480,981 A | 1/1996 | Goodwin et al. | |
| 5,670,527 A | 9/1997 | Adams et al. | |
| 5,677,430 A | 10/1997 | Goodwin et al. | |
| 5,840,869 A | 11/1998 | Mosley et al. | |

FOREIGN PATENT DOCUMENTS

| | | |
|---|---|---|
| EP | 0460846 A | 12/1991 |
| WO | WO 99/40187 | 8/1999 |
| WO | WO 03/043583 A2 | 5/2003 |

OTHER PUBLICATIONS

Giacomelli et al. Serum levels of soluble CD30 are increased in ulcerative colitis (UC) but not in Crohn's disease (CD).. Clin Exp Immunol. Mar. 1998;111(3):532-5.*

Bengtsson Å. et al, "Not only Th2 cells but also Th1 and Th0 cells express CD30 after activation," *J. Leukoc. Biol.* 58:683-689 (1995).

Blom AB et al., "Immune complexes, but not streptococcal cell walls or zymosan, cause chronic arthritis in mouse strains susceptible for collagen type II auto-immune arthritis," *Cytokine* 1999; 11:1046-1056, XP-001089856.

Caligaris-Cappio F. et al., "Circulating levels of soluble CD30, a marker of cells producing Th2-type cytokines, are increased in patients with systemic lupus erythematosus and correlate with disease activity," *Clin. Exp. Rheumatol.* 13:339-343 (1995).

Durkop H. et al., "Molecular cloning and expression of a new member of the nerve growth factor receptor family that is characteristic for Hodgkin's Disease," *Cell* 68:421-427 (1992).

Erickson S. L. et al., "Decreased sensitivity to tumour-necrosis factor but normal T-cell development in TNF receptor-2-deficient mice," *Nature* 372:560-563 (1994).

Gilfillan M. C. et al., "Expression of the costimulatory receptor CD30 is regulated by both CD28 and cytokines," *J. Immunol.* 160:2180-2187 (1998).

Gruss H-J et al., "Biological roles of CD30 ligand in CD30+ malignant lymphomas and T cell-dependent immune responses," *Exp Hematol (Charlottesville)*, 1995, 23:851, XP008005895.

Hamann D. et al., "CD30 expression does not discriminate between human Th1- and Th2-type T cells," *J. Immunol.* 156:1387-1391 (1996).

Horie R. and Watanabe T., "CD30: expression and function in health and disease," *Semin. Immunol.* 10:457-470 (1998).

Joe B. and Wilder R. L., "Animal models of rheumatoid arthritis," *Mol. Med. Today* 5:367-369 (1999).

Joosten et al., Anticytokine Treatment of Established Type II Collagen-Induced Arthritis in DBA/1 Mice, *Arthritis & Rheumatism* 39 (5):797-809, May 1996.

Koon H. B. and Junghans R. P., "Anti-CD30 antibody-based therapy," *Curr. Opin. Oncol.* 12:588-593 (2000).

Körner H. et al., "Tumor necrosis factor blockade in actively induced experimental autoimmune encephalomyelitis prevents clinical disease despite activated T cell infiltration to the central nervous system," *Eur. J. Immunol.* 27:1973-1981 (1997).

(Continued)

*Primary Examiner*—Maher M. Haddad
(74) *Attorney, Agent, or Firm*—Susan E. Lingenfelter

(57) ABSTRACT

The invention provides methods of treating autoimmune and chronic inflammatory conditions by administering agents that hinder the CD30/CD30L interaction, combination treatments, and methods of treating conditions resistant to treatment with TNFα inhibitors by administering agents that inhibit signal transduction by CD30 or IL-1. Included also are treatments involving concurrently administering agents that block the CD30/CD30L interaction and agents that antagonize the IL-4/IL-4R interaction. Additionally provided is an animal model for screening candidate agents for their efficacy in treating conditions that are resistant to treatment with TNFα inhibitors.

13 Claims, No Drawings

OTHER PUBLICATIONS

Körner H. et al., "Critical points of tumor necrosis factor action in central nervous system autoimmune inflammation defined by gene targeting," *J. Exp. Med.* 186(9):1585-1590 (1997).

Kurts C. et al., "Signalling through CD30 protects against autoimmune diabetes mediated by CD8 T cells," *Nature* 398:341-344 (1999).

Liu A. Y. et al., "Chimeric mouse-human IgG1 antibody that can mediate lysis of cancer cells," *Proc. Natl. Acad. Sci. USA* 84:3439-3443 (1987).

Marino M. W. et al., "Characterization of tumor necrosis factor-deficient mice," *Proc. Nat. Acad. Sci. USA* 94:8093-8098 (1997).

Mendel I. et al., "A myelin oligodendrocyte glycoprotein peptide induces typical chronic experimental autoimmune encephalomyelitis in H-$2^b$ mice: fine specificity and T cell receptor Vβ expression of encephalitogenic T cells," *Eur. J. Immunol.* 25:1951-1959 (1995).

Mori L. et al., "Attenuation of collagen-induced arthritis in 55-kDa TNF receptor type 1 (TNFR1)-IgG1-treated and TNFR1-deficient mice," *J. Immunol.* 157:3178-3182 (1996).

Nakamura T. et al., "Reciprocal regulation of CD30 expression on $CD4^+$ T cells by IL-4 and IFN-γ,"*J. Immunol.* 158:2090-2098 (1997).

Peschon J. J. et al., "TNF receptor-deficient mice reveal divergent roles for pp5 and p75 in several models of inflammation," *J. Immunol.* 160:943-952 (1998).

Pfeffer K. et al., "Mice deficient for the 55 kd tumor necrosis factor receptor are resistant to endotoxic shock, yet succumb to L. monocytogenes infection," *Cell* 73:457-467 (1993).

Riechmann L. et al., "Reshaping human antibodies for therapy," *Nature* 332:323-327 (1988).

Romagnani S. et al., "CD30 and type 2 T helper (Th2) responses," *J. Leukoc. Biol.* 57:726-730 (1995).

Romagnani S., "Biology of human $T_H1$ and $T_H2$ cells," *J. Clin. Immunol.* 15(3):121-129 (1995).

Rothe J. et al., "Mice lacking the tumour necrosis factor receptor 1 are resistant to TNF-mediated toxicity but highly susceptible to infection by *Listeria monocytogenes,*" *Nature* 364:798-802 (1993).

Smith C. A. et al., "CD30 antigen, a marker for Hodgkin's lymphoma, is a receptor whose ligand defines an emerging family of cytokines with homology to TNF," *Cell* 73:1349-1360 (1993).

Sundarapandiyan K. et al., "Bispecific antibody-mediated destruction of Hodgkin's lymphoma cells," *J. Immunol. Methods* 248:113-123 (2001).

Wiley S. R. et al., "Reverse signaling via CD30 ligand," *J. Immunol.* 157:3635-3639 (1996).

Winter G. and Harris W. J., "Antibody-based therapy," *TiPS* 14:139-143 (1993).

Yamamoto J. et al., "CD30 expression on circulating memory $CD4^+$ T cells as a Th2-dominated situation in patients with atopic dermatitis," *Allergy* 55:1011-1018 (2000).

* cited by examiner

SEQUENCE LISTING

```
<160> NUMBER OF SEQ ID NOS: 16

<210> SEQ ID NO 1
<211> LENGTH: 705
<212> TYPE: DNA
<213> ORGANISM: Homo sapiens
<220> FEATURE:
<221> NAME/KEY: CDS
<222> LOCATION: (1)..(705)
<223> OTHER INFORMATION:

<400> SEQUENCE: 1 atg gac cca ggg ctg cag caa gca ctc aac gga atg gcc cct cct gga      48
Met Asp Pro Gly Leu Gln Gln Ala Leu Asn Gly Met Ala Pro Pro Gly
1               5                   10                  15 gac aca gcc atg cat gtg ccg gcg ggc tcc gtg gcc agc cac ctg ggg      96
Asp Thr Ala Met His Val Pro Ala Gly Ser Val Ala Ser His Leu Gly
            20                  25                  30 acc acg agc cgc agc tat ttc tat ttg acc aca gcc act ctg gct ctg     144
Thr Thr Ser Arg Ser Tyr Phe Tyr Leu Thr Thr Ala Thr Leu Ala Leu
        35                  40                  45 tgc ctt gtc ttc acg gtg gcc act att atg gtg ttg gtc gtt cag agg     192
Cys Leu Val Phe Thr Val Ala Thr Ile Met Val Leu Val Val Gln Arg
    50                  55                  60 acg gac tcc att ccc aac tca cct gac aac gtc ccc ctc aaa gga gga     240
Thr Asp Ser Ile Pro Asn Ser Pro Asp Asn Val Pro Leu Lys Gly Gly
65                  70                  75                  80 aat tgc tca gaa gac ctc tta tgt atc ctg aaa aga gct cca ttc aag     288
Asn Cys Ser Glu Asp Leu Leu Cys Ile Leu Lys Arg Ala Pro Phe Lys
                85                  90                  95 aag tca tgg gcc tac ctc caa gtg gca aag cat cta aac aaa acc aag     336
Lys Ser Trp Ala Tyr Leu Gln Val Ala Lys His Leu Asn Lys Thr Lys
            100                 105                 110 ttg tct tgg aac aaa gat ggc att ctc cat gga gtc aga tat cag gat     384
Leu Ser Trp Asn Lys Asp Gly Ile Leu His Gly Val Arg Tyr Gln Asp
        115                 120                 125 ggg aat ctg gtg atc caa ttc cct ggt ttg tac ttc atc att tgc caa     432
Gly Asn Leu Val Ile Gln Phe Pro Gly Leu Tyr Phe Ile Ile Cys Gln
    130                 135                 140 ctg cag ttt ctt gta caa tgc cca aat aat tct gtc gat ctg aag ttg     480
Leu Gln Phe Leu Val Gln Cys Pro Asn Asn Ser Val Asp Leu Lys Leu
145                 150                 155                 160 gag ctt ctc atc aac aag cat atc aaa aaa cag gcc ctg gtg aca gtg     528
Glu Leu Leu Ile Asn Lys His Ile Lys Lys Gln Ala Leu Val Thr Val
                165                 170                 175 tgt gag tct gga atg caa acg aaa cac gta tac cag aat ctc tct caa     576
Cys Glu Ser Gly Met Gln Thr Lys His Val Tyr Gln Asn Leu Ser Gln
```

|  |  |  |  |  |  |  |  |  |  |  |  |  |  |  |  |
|---|---|---|---|---|---|---|---|---|---|---|---|---|---|---|---|
|  |  |  | 180 |  |  |  | 185 |  |  |  | 190 |  |  |  |  |
| ttc | ttg | ctg | gat | tac | ctg | cag | gtc | aac | acc | acc | ata | tca | gtc | aat | gtg | 624 |
| Phe | Leu | Leu | Asp | Tyr | Leu | Gln | Val | Asn | Thr | Thr | Ile | Ser | Val | Asn | Val |  |
|  |  | 195 |  |  |  | 200 |  |  |  |  | 205 |  |  |  |  |  |
| gat | aca | ttc | cag | tac | ata | gat | aca | agc | acc | ttt | cct | ctt | gag | aat | gtg | 672 |
| Asp | Thr | Phe | Gln | Tyr | Ile | Asp | Thr | Ser | Thr | Phe | Pro | Leu | Glu | Asn | Val |  |
| 210 |  |  |  |  | 215 |  |  |  |  | 220 |  |  |  |  |  |  |
| ttg | tcc | atc | ttc | tta | tac | agt | aat | tca | gac | tga |  |  |  |  |  | 705 |
| Leu | Ser | Ile | Phe | Leu | Tyr | Ser | Asn | Ser | Asp |  |  |  |  |  |  |  |
| 225 |  |  |  | 230 |  |  |  |  |  |  |  |  |  |  |  |  |

<210> SEQ ID NO 2
<211> LENGTH: 234
<212> TYPE: PRT
<213> ORGANISM: Homo sapiens

<400> SEQUENCE: 2

Met Asp Pro Gly Leu Gln Gln Ala Leu Asn Gly Met Ala Pro Pro Gly
1               5                   10                  15

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
        115                 120                 125

Gly Asn Leu Val Ile Gln Phe Pro Gly Leu Tyr Phe Ile Ile Cys Gln
    130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
        195                 200                 205

Asp Thr Phe Gln Tyr Ile Asp Thr Ser Thr Phe Pro Leu Glu Asn Val
    210                 215                 220

Leu Ser Ile Phe Leu Tyr Ser Asn Ser Asp
225                 230

<210> SEQ ID NO 3
<211> LENGTH: 720
<212> TYPE: DNA
<213> ORGANISM: Mus sp.
<220> FEATURE:
<221> NAME/KEY: CDS
<222> LOCATION: (1)..(720)
<223> OTHER INFORMATION:

<400> SEQUENCE: 3

| | | |
|---|---|---|
| atg gag cca ggg ctg caa caa gca ggc agc tgt ggg gct cct tcc cct<br>Met Glu Pro Gly Leu Gln Gln Ala Gly Ser Cys Gly Ala Pro Ser Pro<br>1                     5                     10                 15 | | 48 |
| gac cca gcc atg cag gtg cag ccc ggc tcg gta gcc agc ccc tgg aga<br>Asp Pro Ala Met Gln Val Gln Pro Gly Ser Val Ala Ser Pro Trp Arg<br>                  20                   25                 30 | | 96 |
| agc acg agg ccc tgg aga agc aca agt cgc agc tac ttc tac ctc agc<br>Ser Thr Arg Pro Trp Arg Ser Thr Ser Arg Ser Tyr Phe Tyr Leu Ser<br>        35                     40                 45 | | 144 |
| acc acc gca ctg gtg tgc ctt gtt gtg gca gtg gcg atc att ctg gta<br>Thr Thr Ala Leu Val Cys Leu Val Val Ala Val Ala Ile Ile Leu Val<br>50                          55                     60 | | 192 |
| ctg gta gtc cag aaa aag gac tcc act cca aat aca act gag aag gcc<br>Leu Val Val Gln Lys Lys Asp Ser Thr Pro Asn Thr Thr Glu Lys Ala<br>65                     70                     75                 80 | | 240 |
| ccc ctt aaa gga gga aat tgc tca gag gat ctc ttc tgt acc ctg aaa<br>Pro Leu Lys Gly Gly Asn Cys Ser Glu Asp Leu Phe Cys Thr Leu Lys<br>                  85                   90                 95 | | 288 |
| agt act cca tcc aag aag tca tgg gcc tac ctc caa gtg tca aag cat<br>Ser Thr Pro Ser Lys Lys Ser Trp Ala Tyr Leu Gln Val Ser Lys His<br>                  100                 105              110 | | 336 |
| ctc aac aat acc aaa ctg tca tgg aac gaa gat ggc acc atc cac gga<br>Leu Asn Asn Thr Lys Leu Ser Trp Asn Glu Asp Gly Thr Ile His Gly<br>                115                 120              125 | | 384 |
| ctc ata tac cag gac ggg aac ctg ata gtc caa ttc cct ggc ttg tac<br>Leu Ile Tyr Gln Asp Gly Asn Leu Ile Val Gln Phe Pro Gly Leu Tyr<br>130                        135                 140 | | 432 |
| ttc atc gtt tgc caa ctg cag ttc ctc gtg cag tgc tca aat cat tct<br>Phe Ile Val Cys Gln Leu Gln Phe Leu Val Gln Cys Ser Asn His Ser<br>145                     150                 155              160 | | 480 |
| gtg gac ctg aca ttg cag ctc ctc atc aat tcc aag atc aaa aag cag<br>Val Asp Leu Thr Leu Gln Leu Leu Ile Asn Ser Lys Ile Lys Lys Gln<br>                 165                 170              175 | | 528 |
| acg ttg gta aca gtg tgt gag tct gga gtt cag agt aag aac atc tac<br>Thr Leu Val Thr Val Cys Glu Ser Gly Val Gln Ser Lys Asn Ile Tyr<br>                 180                 185              190 | | 576 |
| cag aat ctc tct cag ttt ttg ctg cat tac tta cag gtc aac tct acc<br>Gln Asn Leu Ser Gln Phe Leu Leu His Tyr Leu Gln Val Asn Ser Thr<br>                195                 200              205 | | 624 |
| ata tca gtc agg gtg gat aat ttc cag tat gtg gat aca aac act ttc<br>Ile Ser Val Arg Val Asp Asn Phe Gln Tyr Val Asp Thr Asn Thr Phe<br>210                        215                 220 | | 672 |
| cct ctt gat aat gtg cta tcc gtc ttc tta tat agt agc tca gac tga<br>Pro Leu Asp Asn Val Leu Ser Val Phe Leu Tyr Ser Ser Ser Asp<br>225                        230                     235 | | 720 |

<210> SEQ ID NO 4
<211> LENGTH: 239
<212> TYPE: PRT
<213> ORGANISM: Mus sp.

<400> SEQUENCE: 4

Met Glu Pro Gly Leu Gln Gln Ala Gly Ser Cys Gly Ala Pro Ser Pro
1                   5                    10                 15

Asp Pro Ala Met Gln Val Gln Pro Gly Ser Val Ala Ser Pro Trp Arg
                 20                 25                 30

Ser Thr Arg Pro Trp Arg Ser Thr Ser Arg Ser Tyr Phe Tyr Leu Ser
        35                     40                 45

Thr Thr Ala Leu Val Cys Leu Val Val Ala Val Ala Ile Ile Leu Val
50                         55                     60

```
Leu Val Val Gln Lys Lys Asp Ser Thr Pro Asn Thr Thr Glu Lys Ala
 65                  70                  75                  80

Pro Leu Lys Gly Gly Asn Cys Ser Glu Asp Leu Phe Cys Thr Leu Lys
                 85                  90                  95

Ser Thr Pro Ser Lys Lys Ser Trp Ala Tyr Leu Gln Val Ser Lys His
            100                 105                 110

Leu Asn Asn Thr Lys Leu Ser Trp Asn Glu Asp Gly Thr Ile His Gly
        115                 120                 125

Leu Ile Tyr Gln Asp Gly Asn Leu Ile Val Gln Phe Pro Gly Leu Tyr
    130                 135                 140

Phe Ile Val Cys Gln Leu Gln Phe Leu Val Gln Cys Ser Asn His Ser
145                 150                 155                 160

Val Asp Leu Thr Leu Gln Leu Leu Ile Asn Ser Lys Ile Lys Lys Gln
                165                 170                 175

Thr Leu Val Thr Val Cys Glu Ser Gly Val Gln Ser Lys Asn Ile Tyr
            180                 185                 190

Gln Asn Leu Ser Gln Phe Leu Leu His Tyr Leu Gln Val Asn Ser Thr
        195                 200                 205

Ile Ser Val Arg Val Asp Asn Phe Gln Tyr Val Asp Thr Asn Thr Phe
    210                 215                 220

Pro Leu Asp Asn Val Leu Ser Val Phe Leu Tyr Ser Ser Ser Asp
225                 230                 235

<210> SEQ ID NO 5
<211> LENGTH: 1788
<212> TYPE: DNA
<213> ORGANISM: Homo sapiens
<220> FEATURE:
<221> NAME/KEY: CDS
<222> LOCATION: (1)..(1788)
<223> OTHER INFORMATION:

<400> SEQUENCE: 5 atg cgc gtc ctc ctc gcc gcg ctg gga ctg ctg ttc ctg ggg gcg cta      48
Met Arg Val Leu Leu Ala Ala Leu Gly Leu Leu Phe Leu Gly Ala Leu
  1               5                  10                  15 cga gcc ttc cca cag gat cga ccc ttc gag gac acc tgt cat gga aac      96
Arg Ala Phe Pro Gln Asp Arg Pro Phe Glu Asp Thr Cys His Gly Asn
             20                  25                  30 ccc agc cac tac tat gac aag gct gtc agg agg tgc tgt tac cgc tgc     144
Pro Ser His Tyr Tyr Asp Lys Ala Val Arg Arg Cys Cys Tyr Arg Cys
         35                  40                  45 ccc atg ggg ctg ttc ccg aca cag cag tgc cca cag agg cct act gac     192
Pro Met Gly Leu Phe Pro Thr Gln Gln Cys Pro Gln Arg Pro Thr Asp
     50                  55                  60 tgc agg aag cag tgt gag cct gac tac tac ctg gat gag gcc gac cgc     240
Cys Arg Lys Gln Cys Glu Pro Asp Tyr Tyr Leu Asp Glu Ala Asp Arg
 65                  70                  75                  80 tgt aca gcc tgc gtg act tgt tct cga gat gac ctc gtg gag aag acg     288
Cys Thr Ala Cys Val Thr Cys Ser Arg Asp Asp Leu Val Glu Lys Thr
                 85                  90                  95 ccg tgt gca tgg aac tcc tcc cgt gtc tgc gaa tgt cga ccc ggc atg     336
Pro Cys Ala Trp Asn Ser Ser Arg Val Cys Glu Cys Arg Pro Gly Met
            100                 105                 110 ttc tgt tcc acg tct gcc gtc aac tcc tgt gcc cgc tgc ttc ttc cat     384
Phe Cys Ser Thr Ser Ala Val Asn Ser Cys Ala Arg Cys Phe Phe His
        115                 120                 125 tct gtc tgt ccg gca ggg atg att gtc aag ttc cca ggc acg gcg cag     432
```

-continued

| | | | | | | | | | | | | | |
|---|---|---|---|---|---|---|---|---|---|---|---|---|---|
| Ser | Val | Cys | Pro | Ala | Gly | Met | Ile | Val | Lys | Phe | Pro | Gly | Thr | Ala | Gln |
| | 130 | | | | 135 | | | | 140 | | | | |

```
aag aac acg gtc tgt gag ccg gct tcc cca ggg gtc agc cct gcc tgt    480
Lys Asn Thr Val Cys Glu Pro Ala Ser Pro Gly Val Ser Pro Ala Cys
145             150                 155                 160 gcc agc cca gag aac tgc aag gaa ccc tcc agt ggc acc atc ccc cag    528
Ala Ser Pro Glu Asn Cys Lys Glu Pro Ser Ser Gly Thr Ile Pro Gln
                165                 170                 175 gcc aag ccc acc ccg gtg tcc cca gca acc tcc agt gcc agc acc atg    576
Ala Lys Pro Thr Pro Val Ser Pro Ala Thr Ser Ser Ala Ser Thr Met
            180                 185                 190 cct gta aga ggg ggc acc cgc ctc gcc cag gaa gct gct tct aaa ctg    624
Pro Val Arg Gly Gly Thr Arg Leu Ala Gln Glu Ala Ala Ser Lys Leu
        195                 200                 205 acg agg gct ccc gac tct ccc tcc tct gtg gga agg cct agt tca gat    672
Thr Arg Ala Pro Asp Ser Pro Ser Ser Val Gly Arg Pro Ser Ser Asp
    210                 215                 220 cca ggt ctg tcc cca aca cag cca tgc cca gag ggg tct ggt gat tgc    720
Pro Gly Leu Ser Pro Thr Gln Pro Cys Pro Glu Gly Ser Gly Asp Cys
225                 230                 235                 240 aga aag cag tgt gag ccc gac tac tac ctg gac gag gcc ggc cgc tgc    768
Arg Lys Gln Cys Glu Pro Asp Tyr Tyr Leu Asp Glu Ala Gly Arg Cys
                245                 250                 255 aca gcc tgc gtg agc tgt tct cga gat gac ctt gtg gag aag acg cca    816
Thr Ala Cys Val Ser Cys Ser Arg Asp Asp Leu Val Glu Lys Thr Pro
            260                 265                 270 tgt gca tgg aac tcc tcc cgc acc tgc gaa tgt cga cct ggc atg atc    864
Cys Ala Trp Asn Ser Ser Arg Thr Cys Glu Cys Arg Pro Gly Met Ile
        275                 280                 285 tgt gcc aca tca gcc acc aac tcc tgt gcc cgc tgt gtc ccc tac cca    912
Cys Ala Thr Ser Ala Thr Asn Ser Cys Ala Arg Cys Val Pro Tyr Pro
    290                 295                 300 atc tgt gca gga gag acg gtc acc aag ccc cag gat atg gct gag aag    960
Ile Cys Ala Gly Glu Thr Val Thr Lys Pro Gln Asp Met Ala Glu Lys
305                 310                 315                 320 gac acc acc ttt gag gcg cca ccc ctg ggg acc cag ccg gac tgc aac    1008
Asp Thr Thr Phe Glu Ala Pro Pro Leu Gly Thr Gln Pro Asp Cys Asn
                325                 330                 335 ccc acc cca gag aat ggc gag gcg cct gcc agc acc agc ccc act cag    1056
Pro Thr Pro Glu Asn Gly Glu Ala Pro Ala Ser Thr Ser Pro Thr Gln
            340                 345                 350 agc ttg ctg gtg gac tcc cag gcc agt aag acg ctg ccc atc cca acc    1104
Ser Leu Leu Val Asp Ser Gln Ala Ser Lys Thr Leu Pro Ile Pro Thr
        355                 360                 365 agc gct ccc gtc gct ctc tcc tcc acg ggg aag ccc gtt ctg gat gca    1152
Ser Ala Pro Val Ala Leu Ser Ser Thr Gly Lys Pro Val Leu Asp Ala
    370                 375                 380 ggg cca gtg ctc ttc tgg gtg atc ctg gtg ttg gtt gtg gtc ggc        1200
Gly Pro Val Leu Phe Trp Val Ile Leu Val Leu Val Val Val Gly
385                 390                 395                 400 tcc agc gcc ttc ctc ctg tgc cac cgg agg gcc tgc agg aag cga att    1248
Ser Ser Ala Phe Leu Leu Cys His Arg Arg Ala Cys Arg Lys Arg Ile
                405                 410                 415 cgg cag aag ctc cac ctg tgc tac ccg gtc cag acc tcc cag ccc aag    1296
Arg Gln Lys Leu His Leu Cys Tyr Pro Val Gln Thr Ser Gln Pro Lys
            420                 425                 430 cta gag ctt gtg gat tcc aga ccc agg agg agc tca acg cag ctg agg    1344
Leu Glu Leu Val Asp Ser Arg Pro Arg Arg Ser Ser Thr Gln Leu Arg
        435                 440                 445
```

```
                                                                            -continued agt ggt gcg tcg gtg aca gaa ccc gtc gcg gaa gag cga ggg tta atg            1392
Ser Gly Ala Ser Val Thr Glu Pro Val Ala Glu Glu Arg Gly Leu Met
        450                 455                 460 agc cag cca ctg atg gag acc tgc cac agc gtg ggg gca gcc tac ctg            1440
Ser Gln Pro Leu Met Glu Thr Cys His Ser Val Gly Ala Ala Tyr Leu
465                 470                 475                 480 gag agc ctg ccg ctg cag gat gcc agc ccg gcc ggg ggc ccc tcg tcc            1488
Glu Ser Leu Pro Leu Gln Asp Ala Ser Pro Ala Gly Gly Pro Ser Ser
                485                 490                 495 ccc agg gac ctt cct gag ccc cgg gtg tcc acg gag cac acc aat aac            1536
Pro Arg Asp Leu Pro Glu Pro Arg Val Ser Thr Glu His Thr Asn Asn
            500                 505                 510 aag att gag aaa atc tac atc atg aag gct gac acc gtg atc gtg ggg            1584
Lys Ile Glu Lys Ile Tyr Ile Met Lys Ala Asp Thr Val Ile Val Gly
        515                 520                 525 acc gtg aag gct gag ctg ccg gag ggc cgg ggc ctg gcg ggg cca gca            1632
Thr Val Lys Ala Glu Leu Pro Glu Gly Arg Gly Leu Ala Gly Pro Ala
530                 535                 540 gag ccc gag ttg gag gag gag ctg gag gcg gac cat acc ccc cac tac            1680
Glu Pro Glu Leu Glu Glu Glu Leu Glu Ala Asp His Thr Pro His Tyr
545                 550                 555                 560 ccc gag cag gag aca gaa ccg cct ctg ggc agc tgc agc gat gtc atg            1728
Pro Glu Gln Glu Thr Glu Pro Pro Leu Gly Ser Cys Ser Asp Val Met
                565                 570                 575 ctc tca gtg gaa gag gaa ggg aaa gaa gac ccc ttg ccc aca gct gcc            1776
Leu Ser Val Glu Glu Glu Gly Lys Glu Asp Pro Leu Pro Thr Ala Ala
            580                 585                 590 tct gga aag tga                                                            1788
Ser Gly Lys
        595

<210> SEQ ID NO 6
<211> LENGTH: 595
<212> TYPE: PRT
<213> ORGANISM: Homo sapiens

<400> SEQUENCE: 6

Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
            20                  25                  30

Pro Ser His Tyr Tyr Asp Lys Ala Val Arg Arg Cys Cys Tyr Arg Cys
        35                  40                  45

Pro Met Gly Leu Phe Pro Thr Gln Gln Cys Pro Gln Arg Pro Thr Asp
    50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe His
        115                 120                 125

Ser Val Cys Pro Ala Gly Met Ile Val Lys Phe Pro Gly Thr Ala Gln
    130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
```

-continued

```
                165                 170                 175
Ala Lys Pro Thr Pro Val Ser Pro Ala Thr Ser Ser Ala Ser Thr Met
            180                 185                 190
Pro Val Arg Gly Gly Thr Arg Leu Ala Gln Glu Ala Ala Ser Lys Leu
        195                 200                 205
Thr Arg Ala Pro Asp Ser Pro Ser Val Gly Arg Pro Ser Ser Asp
    210                 215                 220
Pro Gly Leu Ser Pro Thr Gln Pro Cys Pro Glu Gly Ser Gly Asp Cys
225                 230                 235                 240
Arg Lys Gln Cys Glu Pro Asp Tyr Tyr Leu Asp Glu Ala Gly Arg Cys
                245                 250                 255
Thr Ala Cys Val Ser Cys Ser Arg Asp Asp Leu Val Glu Lys Thr Pro
            260                 265                 270
Cys Ala Trp Asn Ser Ser Arg Thr Cys Glu Cys Arg Pro Gly Met Ile
        275                 280                 285
Cys Ala Thr Ser Ala Thr Asn Ser Cys Ala Arg Cys Val Pro Tyr Pro
    290                 295                 300
Ile Cys Ala Gly Glu Thr Val Thr Lys Pro Gln Asp Met Ala Glu Lys
305                 310                 315                 320
Asp Thr Thr Phe Glu Ala Pro Pro Leu Gly Thr Gln Pro Asp Cys Asn
                325                 330                 335
Pro Thr Pro Glu Asn Gly Glu Ala Pro Ala Ser Thr Ser Pro Thr Gln
            340                 345                 350
Ser Leu Leu Val Asp Ser Gln Ala Ser Lys Thr Leu Pro Ile Pro Thr
        355                 360                 365
Ser Ala Pro Val Ala Leu Ser Ser Thr Gly Lys Pro Val Leu Asp Ala
    370                 375                 380
Gly Pro Val Leu Phe Trp Val Ile Leu Val Leu Val Val Val Val Gly
385                 390                 395                 400
Ser Ser Ala Phe Leu Leu Cys His Arg Arg Ala Cys Arg Lys Arg Ile
                405                 410                 415
Arg Gln Lys Leu His Leu Cys Tyr Pro Val Gln Thr Ser Gln Pro Lys
            420                 425                 430
Leu Glu Leu Val Asp Ser Arg Pro Arg Arg Ser Ser Thr Gln Leu Arg
        435                 440                 445
Ser Gly Ala Ser Val Thr Glu Pro Val Ala Glu Glu Arg Gly Leu Met
    450                 455                 460
Ser Gln Pro Leu Met Glu Thr Cys His Ser Val Gly Ala Ala Tyr Leu
465                 470                 475                 480
Glu Ser Leu Pro Leu Gln Asp Ala Ser Pro Ala Gly Gly Pro Ser Ser
                485                 490                 495
Pro Arg Asp Leu Pro Glu Pro Arg Val Ser Thr Glu His Thr Asn Asn
            500                 505                 510
Lys Ile Glu Lys Ile Tyr Ile Met Lys Ala Asp Thr Val Ile Val Gly
        515                 520                 525
Thr Val Lys Ala Glu Leu Pro Glu Gly Arg Gly Leu Ala Gly Pro Ala
    530                 535                 540
Glu Pro Glu Leu Glu Glu Glu Leu Glu Ala Asp His Thr Pro His Tyr
545                 550                 555                 560
Pro Glu Gln Glu Thr Glu Pro Pro Leu Gly Ser Cys Ser Asp Val Met
                565                 570                 575
Leu Ser Val Glu Glu Glu Gly Lys Glu Asp Pro Leu Pro Thr Ala Ala
            580                 585                 590
```

```
Ser Gly Lys
        595

<210> SEQ ID NO 7
<211> LENGTH: 1357
<212> TYPE: DNA
<213> ORGANISM: Homo sapiens
<220> FEATURE:
<221> NAME/KEY: mat_peptide
<222> LOCATION: (193)..()
<223> OTHER INFORMATION:
<220> FEATURE:
<221> NAME/KEY: CDS
<222> LOCATION: (154)..(1347)
<223> OTHER INFORMATION:
<220> FEATURE:
<221> NAME/KEY: sig_peptide
<222> LOCATION: (154)..(192)
<223> OTHER INFORMATION:

<400> SEQUENCE: 7
ctggaaaata cattctgcta ctcttaaaaa ctagtgacgc tcatacaaat caacagaaag    60
agcttctgaa ggaagacttt aaagctgctt ctgccacgtg ctgctgggtc tcagtcctcc   120
acttcccgtg tcctctggaa gttgtcagga gca atg ttg cgc ttg tac gtg ttg   174
                                 Met Leu Arg Leu Tyr Val Leu
                                                    -10 gta atg gga gtt tct gcc ttc acc ctt cag cct gcg gca cac aca ggg    222
Val Met Gly Val Ser Ala Phe Thr Leu Gln Pro Ala Ala His Thr Gly
    -5              -1   1               5                  10 gct gcc aga agc tgc cgg ttt cgt ggg agg cat tac aag cgg gag ttc    270
Ala Ala Arg Ser Cys Arg Phe Arg Gly Arg His Tyr Lys Arg Glu Phe
                 15                  20                  25 agg ctg gaa ggg gag cct gta gcc ctg agg tgc ccc cag gtg ccc tac    318
Arg Leu Glu Gly Glu Pro Val Ala Leu Arg Cys Pro Gln Val Pro Tyr
         30                  35                  40 tgg ttg tgg gcc tct gtc agc ccc cgc atc aac ctg aca tgg cat aaa    366
Trp Leu Trp Ala Ser Val Ser Pro Arg Ile Asn Leu Thr Trp His Lys
     45                  50                  55 aat gac tct gct agg acg gtc cca gga gaa gaa gag aca cgg atg tgg    414
Asn Asp Ser Ala Arg Thr Val Pro Gly Glu Glu Glu Thr Arg Met Trp
 60                  65                  70 gcc cag gac ggt gct ctg tgg ctt ctg cca gcc ttg cag gag gac tct    462
Ala Gln Asp Gly Ala Leu Trp Leu Leu Pro Ala Leu Gln Glu Asp Ser
 75                  80                  85                  90 ggc acc tac gtc tgc act act aga aat gct tct tac tgt gac aaa atg    510
Gly Thr Tyr Val Cys Thr Thr Arg Asn Ala Ser Tyr Cys Asp Lys Met
                 95                 100                 105 tcc att gag ctc aga gtt ttt gag aat aca gat gct ttc ctg ccg ttc    558
Ser Ile Glu Leu Arg Val Phe Glu Asn Thr Asp Ala Phe Leu Pro Phe
             110                 115                 120 atc tca tac ccg caa att tta acc ttg tca acc tct ggg gta tta gta    606
Ile Ser Tyr Pro Gln Ile Leu Thr Leu Ser Thr Ser Gly Val Leu Val
         125                 130                 135 tgc cct gac ctg agt gaa ttc acc cgt gac aaa act gac gtg aag att    654
Cys Pro Asp Leu Ser Glu Phe Thr Arg Asp Lys Thr Asp Val Lys Ile
     140                 145                 150 caa tgg tac aag gat tct ctt ctt ttt gat aaa gac aat gag aaa ttt    702
Gln Trp Tyr Lys Asp Ser Leu Leu Phe Asp Lys Asp Asn Glu Lys Phe
155                 160                 165                 170 cta agt gtg agg ggg acc act cac tta ctc gta cac gat gtg gcc ctg    750
Leu Ser Val Arg Gly Thr Thr His Leu Leu Val His Asp Val Ala Leu
                175                 180                 185
```

```
gaa gat gct ggc tat tac cgc tgt gtc ctg aca ttt gcc cat gaa ggc      798
Glu Asp Ala Gly Tyr Tyr Arg Cys Val Leu Thr Phe Ala His Glu Gly
        190                 195                 200 cag caa tac aac atc act agg agt att gag cta cgc atc aag aaa aaa      846
Gln Gln Tyr Asn Ile Thr Arg Ser Ile Glu Leu Arg Ile Lys Lys Lys
205                 210                 215 aaa gaa gag acc att cct gtg atc att tcc ccc ctc aag acc ata tca      894
Lys Glu Glu Thr Ile Pro Val Ile Ile Ser Pro Leu Lys Thr Ile Ser
220                 225                 230 gct tct ctg ggg tca aga ctg aca atc ccg tgt aag gtg ttt ctg gga      942
Ala Ser Leu Gly Ser Arg Leu Thr Ile Pro Cys Lys Val Phe Leu Gly
235                 240                 245                 250 acc ggc aca ccc tta acc acc atg ctg tgg tgg acg gcc aat gac acc      990
Thr Gly Thr Pro Leu Thr Thr Met Leu Trp Trp Thr Ala Asn Asp Thr
            255                 260                 265 cac ata gag agc gcc tac ccg gga ggc cgc gtg acc gag ggg cca cgc     1038
His Ile Glu Ser Ala Tyr Pro Gly Gly Arg Val Thr Glu Gly Pro Arg
            270                 275                 280 cag gaa tat tca gaa aat aat gag aac tac att gaa gtg cca ttg att     1086
Gln Glu Tyr Ser Glu Asn Asn Glu Asn Tyr Ile Glu Val Pro Leu Ile
            285                 290                 295 ttt gat cct gtc aca aga gag gat ttg cac atg gat ttt aaa tgt gtt     1134
Phe Asp Pro Val Thr Arg Glu Asp Leu His Met Asp Phe Lys Cys Val
300                 305                 310 gtc cat aat acc ctg agt ttt cag aca cta cgc acc aca gtc aag gaa     1182
Val His Asn Thr Leu Ser Phe Gln Thr Leu Arg Thr Thr Val Lys Glu
315                 320                 325                 330 gcc tcc tcc acg ttc tcc tgg ggc att gtg ctg gcc cca ctt tca ctg     1230
Ala Ser Ser Thr Phe Ser Trp Gly Ile Val Leu Ala Pro Leu Ser Leu
                335                 340                 345 gcc ttc ttg gtt ttg ggg gga ata tgg atg cac aga cgg tgc aaa cac     1278
Ala Phe Leu Val Leu Gly Gly Ile Trp Met His Arg Arg Cys Lys His
            350                 355                 360 aga act gga aaa gca gat ggt ctg act gtg cta tgg cct cat cat caa     1326
Arg Thr Gly Lys Ala Asp Gly Leu Thr Val Leu Trp Pro His His Gln
            365                 370                 375 gac ttt caa tcc tat ccc aag tgaaataaat                              1357
Asp Phe Gln Ser Tyr Pro Lys
380                 385

<210> SEQ ID NO 8
<211> LENGTH: 398
<212> TYPE: PRT
<213> ORGANISM: Homo sapiens

<400> SEQUENCE: 8

Met Leu Arg Leu Tyr Val Leu Val Met Gly Val Ser Ala Phe Thr Leu
            -10                 -5              -1   1

Gln Pro Ala Ala His Thr Gly Ala Ala Arg Ser Cys Arg Phe Arg Gly
        5                   10                  15

Arg His Tyr Lys Arg Glu Phe Arg Leu Glu Gly Glu Pro Val Ala Leu
20                  25                  30                  35

Arg Cys Pro Gln Val Pro Tyr Trp Leu Trp Ala Ser Val Ser Pro Arg
                40                  45                  50

Ile Asn Leu Thr Trp His Lys Asn Asp Ser Ala Arg Thr Val Pro Gly
            55                  60                  65

Glu Glu Glu Thr Arg Met Trp Ala Gln Asp Gly Ala Leu Trp Leu Leu
        70                  75                  80
```

```
Pro Ala Leu Gln Glu Asp Ser Gly Thr Tyr Val Cys Thr Thr Arg Asn
 85                  90                  95

Ala Ser Tyr Cys Asp Lys Met Ser Ile Glu Leu Arg Val Phe Glu Asn
100                 105                 110                 115

Thr Asp Ala Phe Leu Pro Phe Ile Ser Tyr Pro Gln Ile Leu Thr Leu
                120                 125                 130

Ser Thr Ser Gly Val Leu Val Cys Pro Asp Leu Ser Glu Phe Thr Arg
            135                 140                 145

Asp Lys Thr Asp Val Lys Ile Gln Trp Tyr Lys Asp Ser Leu Leu Leu
        150                 155                 160

Asp Lys Asp Asn Glu Lys Phe Leu Ser Val Arg Gly Thr Thr His Leu
    165                 170                 175

Leu Val His Asp Val Ala Leu Glu Asp Ala Gly Tyr Tyr Arg Cys Val
180                 185                 190                 195

Leu Thr Phe Ala His Glu Gly Gln Gln Tyr Asn Ile Thr Arg Ser Ile
                200                 205                 210

Glu Leu Arg Ile Lys Lys Lys Glu Glu Thr Ile Pro Val Ile Ile
                215                 220                 225

Ser Pro Leu Lys Thr Ile Ser Ala Ser Leu Gly Ser Arg Leu Thr Ile
            230                 235                 240

Pro Cys Lys Val Phe Leu Gly Thr Gly Thr Pro Leu Thr Thr Met Leu
245                 250                 255

Trp Trp Thr Ala Asn Asp Thr His Ile Glu Ser Ala Tyr Pro Gly Gly
260                 265                 270                 275

Arg Val Thr Glu Gly Pro Arg Gln Glu Tyr Ser Glu Asn Asn Glu Asn
                280                 285                 290

Tyr Ile Glu Val Pro Leu Ile Phe Asp Pro Val Thr Arg Glu Asp Leu
            295                 300                 305

His Met Asp Phe Lys Cys Val Val His Asn Thr Leu Ser Phe Gln Thr
                310                 315                 320

Leu Arg Thr Thr Val Lys Glu Ala Ser Ser Thr Phe Ser Trp Gly Ile
            325                 330                 335

Val Leu Ala Pro Leu Ser Leu Ala Phe Leu Val Leu Gly Gly Ile Trp
340                 345                 350                 355

Met His Arg Arg Cys Lys His Arg Thr Gly Lys Ala Asp Gly Leu Thr
                360                 365                 370

Val Leu Trp Pro His His Gln Asp Phe Gln Ser Tyr Pro Lys
            375                 380                 385

<210> SEQ ID NO 9
<211> LENGTH: 23
<212> TYPE: DNA
<213> ORGANISM: Artificial Sequence
<220> FEATURE:
<223> OTHER INFORMATION: Synthetic primer

<400> SEQUENCE: 9
ggattgtcac ggtgccgttg aag                                    23

<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
```

-continued

```
ccggtggatg tggaatgtgt g                                            21

<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
tgctgatggg gatacatcca tc                                           22

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
ccggtggatg tggaatgtgt g                                            21

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
agagctccag gcacaagggc                                              20

<210> SEQ ID NO 14
<211> LENGTH: 19
<212> TYPE: DNA
<213> ORGANISM: Artificial Sequence
<220> FEATURE:
<223> OTHER INFORMATION: Synthetic primer

<400> SEQUENCE: 14
aacgggccag acctcgggt                                               19

<210> SEQ ID NO 15
<211> LENGTH: 2478
<212> TYPE: DNA
<213> ORGANISM: Homo sapiens
<220> FEATURE:
<221> NAME/KEY: CDS
<222> LOCATION: (1)..(2475)
<223> OTHER INFORMATION:
<220> FEATURE:
<221> NAME/KEY: mat_peptide
<222> LOCATION: (76)..()
<223> OTHER INFORMATION:

<400> SEQUENCE: 15 atg ggg tgg ctt tgc tct ggg ctc ctg ttc cct gtg agc tgc ctg gtc    48
Met Gly Trp Leu Cys Ser Gly Leu Leu Phe Pro Val Ser Cys Leu Val
-25              -20                 -15                 -10 ctg ctg cag gtg gca agc tct ggg aac atg aag gtc ttg cag gag ccc    96
Leu Leu Gln Val Ala Ser Ser Gly Asn Met Lys Val Leu Gln Glu Pro
            -5                  -1   1                   5 acc tgc gtc tcc gac tac atg agc atc tct act tgc gag tgg aag atg   144
Thr Cys Val Ser Asp Tyr Met Ser Ile Ser Thr Cys Glu Trp Lys Met
        10                  15                  20 aat ggt ccc acc aat tgc agc acc gag ctc cgc ctg ttg tac cag ctg   192
```

```
            Asn Gly Pro Thr Asn Cys Ser Thr Glu Leu Arg Leu Leu Tyr Gln Leu
                 25                  30                  35 gtt ttt ctg ctc tcc gaa gcc cac acg tgt atc cct gag aac aac gga              240
Val Phe Leu Leu Ser Glu Ala His Thr Cys Ile Pro Glu Asn Asn Gly
 40                  45                  50                  55 ggc gcg ggg tgc gtg tgc cac ctg ctc atg gat gac gtg gtc agt gcg              288
Gly Ala Gly Cys Val Cys His Leu Leu Met Asp Asp Val Val Ser Ala
                 60                  65                  70 gat aac tat aca ctg gac ctg tgg gct ggg cag cag ctg ctg tgg aag              336
Asp Asn Tyr Thr Leu Asp Leu Trp Ala Gly Gln Gln Leu Leu Trp Lys
         75                  80                  85 ggc tcc ttc aag ccc agc gag cat gtg aaa ccc agg gcc cca gga aac              384
Gly Ser Phe Lys Pro Ser Glu His Val Lys Pro Arg Ala Pro Gly Asn
             90                  95                 100 ctg aca gtt cac acc aat gtc tcc gac act ctg ctg ctg acc tgg agc              432
Leu Thr Val His Thr Asn Val Ser Asp Thr Leu Leu Leu Thr Trp Ser
        105                 110                 115 aac ccg tat ccc cct gac aat tac ctg tat aat cat ctc acc tat gca              480
Asn Pro Tyr Pro Pro Asp Asn Tyr Leu Tyr Asn His Leu Thr Tyr Ala
120                 125                 130                 135 gtc aac att tgg agt gaa aac gac ccg gca gat ttc aga atc tat aac              528
Val Asn Ile Trp Ser Glu Asn Asp Pro Ala Asp Phe Arg Ile Tyr Asn
                140                 145                 150 gtg acc tac cta gaa ccc tcc ctc cgc atc gca gcc agc acc ctg aag              576
Val Thr Tyr Leu Glu Pro Ser Leu Arg Ile Ala Ala Ser Thr Leu Lys
        155                 160                 165 tct ggg att tcc tac agg gca cgg gtg agg gcc tgg gct cag tgc tat              624
Ser Gly Ile Ser Tyr Arg Ala Arg Val Arg Ala Trp Ala Gln Cys Tyr
        170                 175                 180 aac acc acc tgg agt gag tgg agc ccc agc acc aag tgg cac aac tcc              672
Asn Thr Thr Trp Ser Glu Trp Ser Pro Ser Thr Lys Trp His Asn Ser
        185                 190                 195 tac agg gag ccc ttc gag cag cac ctc ctg ctg ggc gtc agc gtt tcc              720
Tyr Arg Glu Pro Phe Glu Gln His Leu Leu Leu Gly Val Ser Val Ser
200                 205                 210                 215 tgc att gtc atc ctg gcc gtc tgc ctg ttg tgc tat gtc agc atc acc              768
Cys Ile Val Ile Leu Ala Val Cys Leu Leu Cys Tyr Val Ser Ile Thr
                220                 225                 230 aag att aag aaa gaa tgg tgg gat cag att ccc aac cca gcc cgc agc              816
Lys Ile Lys Lys Glu Trp Trp Asp Gln Ile Pro Asn Pro Ala Arg Ser
        235                 240                 245 cgc ctc gtg gct ata ata atc cag gat gct cag ggg tca cag tgg gag              864
Arg Leu Val Ala Ile Ile Ile Gln Asp Ala Gln Gly Ser Gln Trp Glu
        250                 255                 260 aag cgg tcc cga ggc cag gaa cca gcc aag tgc cca cac tgg aag aat              912
Lys Arg Ser Arg Gly Gln Glu Pro Ala Lys Cys Pro His Trp Lys Asn
        265                 270                 275 tgt ctt acc aag ctc ttg ccc tgt ttt ctg gag cac aac atg aaa agg              960
Cys Leu Thr Lys Leu Leu Pro Cys Phe Leu Glu His Asn Met Lys Arg
280                 285                 290                 295 gat gaa gat cct cac aag gct gcc aaa gag atg cct ttc cag ggc tct             1008
Asp Glu Asp Pro His Lys Ala Ala Lys Glu Met Pro Phe Gln Gly Ser
                300                 305                 310 gga aaa tca gca tgg tgc cca gtg gag atc agc aag aca gtc ctc tgg             1056
Gly Lys Ser Ala Trp Cys Pro Val Glu Ile Ser Lys Thr Val Leu Trp
        315                 320                 325 cca gag agc atc agc gtg gtg cga tgt gtg gag ttg ttt gag gcc ccg             1104
Pro Glu Ser Ile Ser Val Val Arg Cys Val Glu Leu Phe Glu Ala Pro
        330                 335                 340
```

```
gtg gag tgt gag gag gag gag gtg gag gaa gaa aaa ggg agc ttc      1152
Val Glu Cys Glu Glu Glu Glu Val Glu Glu Glu Lys Gly Ser Phe
345                 350                 355 tgt gca tcg cct gag agc agc agg gat gac ttc cag gag gga agg gag  1200
Cys Ala Ser Pro Glu Ser Ser Arg Asp Asp Phe Gln Glu Gly Arg Glu
360                 365                 370                 375 ggc att gtg gcc cgg cta aca gag agc ctg ttc ctg gac ctg ctc gga  1248
Gly Ile Val Ala Arg Leu Thr Glu Ser Leu Phe Leu Asp Leu Leu Gly
                380                 385                 390 gag gag aat ggg ggc ttt tgc cag cag gac atg ggg gag tca tgc ctt  1296
Glu Glu Asn Gly Gly Phe Cys Gln Gln Asp Met Gly Glu Ser Cys Leu
            395                 400                 405 ctt cca cct tcg gga agt acg agt gct cac atg ccc tgg gat gag ttc  1344
Leu Pro Pro Ser Gly Ser Thr Ser Ala His Met Pro Trp Asp Glu Phe
        410                 415                 420 cca agt gca ggg ccc aag gag gca cct ccc tgg ggc aag gag cag cct  1392
Pro Ser Ala Gly Pro Lys Glu Ala Pro Pro Trp Gly Lys Glu Gln Pro
    425                 430                 435 ctc cac ctg gag cca agt cct cct gcc agc ccg acc cag agt cca gac  1440
Leu His Leu Glu Pro Ser Pro Pro Ala Ser Pro Thr Gln Ser Pro Asp
440                 445                 450                 455 aac ctg act tgc aca gag acg ccc ctc gtc atc gca ggc aac cct gct  1488
Asn Leu Thr Cys Thr Glu Thr Pro Leu Val Ile Ala Gly Asn Pro Ala
                460                 465                 470 tac cgc agc ttc agc aac tcc ctg agc cag tca ccg tgt ccc aga gag  1536
Tyr Arg Ser Phe Ser Asn Ser Leu Ser Gln Ser Pro Cys Pro Arg Glu
            475                 480                 485 ctg ggt cca gac cca ctg ctg gcc aga cac ctg gag gaa gta gaa ccc  1584
Leu Gly Pro Asp Pro Leu Leu Ala Arg His Leu Glu Glu Val Glu Pro
        490                 495                 500 gag atg ccc tgt gtc ccc cag ctc tct gag cca acc act gtg ccc caa  1632
Glu Met Pro Cys Val Pro Gln Leu Ser Glu Pro Thr Thr Val Pro Gln
    505                 510                 515 cct gag cca gaa acc tgg gag cag atc ctc cgc cga aat gtc ctc cag  1680
Pro Glu Pro Glu Thr Trp Glu Gln Ile Leu Arg Arg Asn Val Leu Gln
520                 525                 530                 535 cat ggg gca gct gca gcc ccc gtc tcg gcc ccc acc agt ggc tat cag  1728
His Gly Ala Ala Ala Ala Pro Val Ser Ala Pro Thr Ser Gly Tyr Gln
                540                 545                 550 gag ttt gta cat gcg gtg gag cag ggt ggc acc cag gcc agt gcg gtg  1776
Glu Phe Val His Ala Val Glu Gln Gly Gly Thr Gln Ala Ser Ala Val
            555                 560                 565 gtg ggc ttg ggt ccc cca gga gag gct ggt tac aag gcc ttc tca agc  1824
Val Gly Leu Gly Pro Pro Gly Glu Ala Gly Tyr Lys Ala Phe Ser Ser
        570                 575                 580 ctg ctt gcc agc agt gct gtg tcc cca gag aaa tgt ggg ttt ggg gct  1872
Leu Leu Ala Ser Ser Ala Val Ser Pro Glu Lys Cys Gly Phe Gly Ala
    585                 590                 595 agc agt ggg gaa gag ggg tat aag cct ttc caa gac ctc att cct ggc  1920
Ser Ser Gly Glu Glu Gly Tyr Lys Pro Phe Gln Asp Leu Ile Pro Gly
600                 605                 610                 615 tgc cct ggg gac cct gcc cca gtc cct gtc ccc ttg ttc acc ttt gga  1968
Cys Pro Gly Asp Pro Ala Pro Val Pro Val Pro Leu Phe Thr Phe Gly
                620                 625                 630 ctg gac agg gag cca cct cgc agt ccg cag agc tca cat ctc cca agc  2016
Leu Asp Arg Glu Pro Pro Arg Ser Pro Gln Ser Ser His Leu Pro Ser
            635                 640                 645 agc tcc cca gag cac ctg ggt ctg gag ccg ggg gaa aag gta gag gac  2064
Ser Ser Pro Glu His Leu Gly Leu Glu Pro Gly Glu Lys Val Glu Asp
        650                 655                 660
```

-continued

```
atg cca aag ccc cca ctt ccc cag gag cag gcc aca gac ccc ctt gtg        2112
Met Pro Lys Pro Pro Leu Pro Gln Glu Gln Ala Thr Asp Pro Leu Val
    665                 670                 675 gac agc ctg ggc agt ggc att gtc tac tca gcc ctt acc tgc cac ctg        2160
Asp Ser Leu Gly Ser Gly Ile Val Tyr Ser Ala Leu Thr Cys His Leu
680                 685                 690                 695 tgc ggc cac ctg aaa cag tgt cat ggc cag gag gat ggt ggc cag acc        2208
Cys Gly His Leu Lys Gln Cys His Gly Gln Glu Asp Gly Gly Gln Thr
                700                 705                 710 cct gtc atg gcc agt cct tgc tgt ggc tgc tgt gga gac agg tcc            2256
Pro Val Met Ala Ser Pro Cys Cys Gly Cys Cys Gly Asp Arg Ser
            715                 720                 725 tcg ccc cct aca acc ccc ctg agg gcc cca gac ccc tct cca ggt ggg        2304
Ser Pro Pro Thr Thr Pro Leu Arg Ala Pro Asp Pro Ser Pro Gly Gly
            730                 735                 740 gtt cca ctg gag gcc agt ctg tgt ccg gcc tcc ctg gca ccc tcg ggc        2352
Val Pro Leu Glu Ala Ser Leu Cys Pro Ala Ser Leu Ala Pro Ser Gly
745                 750                 755 atc tca gag aag agt aaa tcc tca tca tcc ttc cat cct gcc cct ggc        2400
Ile Ser Glu Lys Ser Lys Ser Ser Ser Ser Phe His Pro Ala Pro Gly
760                 765                 770                 775 aat gct cag agc tca agc cag acc ccc aaa atc gtg aac ttt gtc tcc        2448
Asn Ala Gln Ser Ser Ser Gln Thr Pro Lys Ile Val Asn Phe Val Ser
                780                 785                 790 gtg gga ccc aca tac atg agg gtc tct tat                                2478
Val Gly Pro Thr Tyr Met Arg Val Ser
            795                 800

<210> SEQ ID NO 16
<211> LENGTH: 825
<212> TYPE: PRT
<213> ORGANISM: Homo sapiens

<400> SEQUENCE: 16

Met Gly Trp Leu Cys Ser Gly Leu Leu Phe Pro Val Ser Cys Leu Val
-25                 -20                 -15                 -10

Leu Leu Gln Val Ala Ser Ser Gly Asn Met Lys Val Leu Gln Glu Pro
                -5                  -1  1               5

Thr Cys Val Ser Asp Tyr Met Ser Ile Ser Thr Cys Glu Trp Lys Met
            10                  15                  20

Asn Gly Pro Thr Asn Cys Ser Thr Glu Leu Arg Leu Leu Tyr Gln Leu
        25                  30                  35

Val Phe Leu Leu Ser Glu Ala His Thr Cys Ile Pro Glu Asn Asn Gly
40                  45                  50                  55

Gly Ala Gly Cys Val Cys His Leu Leu Met Asp Asp Val Val Ser Ala
                60                  65                  70

Asp Asn Tyr Thr Leu Asp Leu Trp Ala Gly Gln Gln Leu Leu Trp Lys
            75                  80                  85

Gly Ser Phe Lys Pro Ser Glu His Val Lys Pro Arg Ala Pro Gly Asn
        90                  95                  100

Leu Thr Val His Thr Asn Val Ser Asp Thr Leu Leu Leu Thr Trp Ser
    105                 110                 115

Asn Pro Tyr Pro Pro Asp Asn Tyr Leu Tyr Asn His Leu Thr Tyr Ala
120                 125                 130                 135

Val Asn Ile Trp Ser Glu Asn Asp Pro Ala Asp Phe Arg Ile Tyr Asn
                140                 145                 150

Val Thr Tyr Leu Glu Pro Ser Leu Arg Ile Ala Ala Ser Thr Leu Lys
```

-continued

```
            155                 160                 165
Ser Gly Ile Ser Tyr Arg Ala Arg Val Arg Ala Trp Ala Gln Cys Tyr
        170                 175                 180

Asn Thr Thr Trp Ser Glu Trp Ser Pro Ser Thr Lys Trp His Asn Ser
185                 190                 195

Tyr Arg Glu Pro Phe Glu Gln His Leu Leu Gly Val Ser Val Ser
200                 205                 210                 215

Cys Ile Val Ile Leu Ala Val Cys Leu Leu Cys Tyr Val Ser Ile Thr
                220                 225                 230

Lys Ile Lys Lys Glu Trp Trp Asp Gln Ile Pro Asn Pro Ala Arg Ser
            235                 240                 245

Arg Leu Val Ala Ile Ile Gln Asp Ala Gln Gly Ser Gln Trp Glu
        250                 255                 260

Lys Arg Ser Arg Gly Gln Glu Pro Ala Lys Cys Pro His Trp Lys Asn
        265                 270                 275

Cys Leu Thr Lys Leu Leu Pro Cys Phe Leu Glu His Asn Met Lys Arg
280                 285                 290                 295

Asp Glu Asp Pro His Lys Ala Ala Lys Glu Met Pro Phe Gln Gly Ser
                300                 305                 310

Gly Lys Ser Ala Trp Cys Pro Val Glu Ile Ser Lys Thr Val Leu Trp
            315                 320                 325

Pro Glu Ser Ile Ser Val Val Arg Cys Val Glu Leu Phe Glu Ala Pro
        330                 335                 340

Val Glu Cys Glu Glu Glu Glu Val Glu Glu Lys Gly Ser Phe
        345                 350                 355

Cys Ala Ser Pro Glu Ser Ser Arg Asp Asp Phe Gln Glu Gly Arg Glu
360                 365                 370                 375

Gly Ile Val Ala Arg Leu Thr Glu Ser Leu Phe Leu Asp Leu Leu Gly
                380                 385                 390

Glu Glu Asn Gly Gly Phe Cys Gln Gln Asp Met Gly Glu Ser Cys Leu
            395                 400                 405

Leu Pro Pro Ser Gly Ser Thr Ser Ala His Met Pro Trp Asp Glu Phe
        410                 415                 420

Pro Ser Ala Gly Pro Lys Glu Ala Pro Pro Trp Gly Lys Glu Gln Pro
425                 430                 435

Leu His Leu Glu Pro Ser Pro Ala Ser Pro Thr Gln Ser Pro Asp
440                 445                 450                 455

Asn Leu Thr Cys Thr Glu Thr Pro Leu Val Ile Ala Gly Asn Pro Ala
                460                 465                 470

Tyr Arg Ser Phe Ser Asn Ser Leu Ser Gln Ser Pro Cys Pro Arg Glu
            475                 480                 485

Leu Gly Pro Asp Pro Leu Leu Ala Arg His Leu Glu Glu Val Glu Pro
        490                 495                 500

Glu Met Pro Cys Val Pro Gln Leu Ser Glu Pro Thr Thr Val Pro Gln
        505                 510                 515

Pro Glu Pro Glu Thr Trp Glu Gln Ile Leu Arg Arg Asn Val Leu Gln
520                 525                 530                 535

His Gly Ala Ala Ala Pro Val Ser Ala Pro Thr Ser Gly Tyr Gln
                540                 545                 550

Glu Phe Val His Ala Val Glu Gln Gly Gly Thr Gln Ala Ser Ala Val
            555                 560                 565

Val Gly Leu Gly Pro Pro Gly Glu Ala Gly Tyr Lys Ala Phe Ser Ser
        570                 575                 580
```

-continued

```
Leu Leu Ala Ser Ser Ala Val Ser Pro Glu Lys Cys Gly Phe Gly Ala
    585                 590                 595

Ser Ser Gly Glu Glu Gly Tyr Lys Pro Phe Gln Asp Leu Ile Pro Gly
600                 605                 610                 615

Cys Pro Gly Asp Pro Ala Pro Val Pro Val Pro Leu Phe Thr Phe Gly
                620                 625                 630

Leu Asp Arg Glu Pro Pro Arg Ser Pro Gln Ser Ser His Leu Pro Ser
            635                 640                 645

Ser Ser Pro Glu His Leu Gly Leu Glu Pro Gly Glu Lys Val Glu Asp
        650                 655                 660

Met Pro Lys Pro Pro Leu Pro Gln Glu Gln Ala Thr Asp Pro Leu Val
    665                 670                 675

Asp Ser Leu Gly Ser Gly Ile Val Tyr Ser Ala Leu Thr Cys His Leu
680                 685                 690                 695

Cys Gly His Leu Lys Gln Cys His Gly Gln Glu Asp Gly Gly Gln Thr
                700                 705                 710

Pro Val Met Ala Ser Pro Cys Cys Gly Cys Cys Cys Gly Asp Arg Ser
            715                 720                 725

Ser Pro Pro Thr Thr Pro Leu Arg Ala Pro Asp Pro Ser Pro Gly Gly
        730                 735                 740

Val Pro Leu Glu Ala Ser Leu Cys Pro Ala Ser Leu Ala Pro Ser Gly
    745                 750                 755

Ile Ser Glu Lys Ser Lys Ser Ser Ser Phe His Pro Ala Pro Gly
760                 765                 770                 775

Asn Ala Gln Ser Ser Ser Gln Thr Pro Lys Ile Val Asn Phe Val Ser
                780                 785                 790

Val Gly Pro Thr Tyr Met Arg Val Ser
            795                 800
```

METHODS FOR TREATING AUTOIMMUNE AND CHRONIC INFLAMMATORY CONDITIONS USING ANTAGONISTS OF CD30 OR CD30L

CROSS REFERENCE TO RELATED APPLICATIONS

This application is a divisional of U.S. patent application Ser. No. 10/648,136, filed Aug. 26, 2003, now U.S. Pat. No. 7,122,183, issued Oct. 17, 2006, which is a divisional of U.S. patent application Ser. No. 09/921,667 filed on Aug. 3, 2001, now U.S. Pat. No. 6,652,854, issued Nov. 25, 2003, which claims the benefit of priority from U.S. patent application 60/224,079, filed Aug. 8, 2000.

FIELD OF THE INVENTION

This invention relates generally to methods for treating autoimmune and inflammatory disorders that involve administering agents that block the interaction between CD30 and CD30L or IL-1 and IL-1R1, and also provides an animal model for testing the ability of a compound to treat inflammatory conditions that respond poorly to treatment with TNFα inhibitors.

BACKGROUND OF THE INVENTION

CD30 and its ligand, CD30L, are membrane proteins of the TNFR and TNF ligand superfamilies, respectively, and are expressed on various lymphoid and myeloid cells. CD30 was first described as an antigen on Hodgkin's disease cells, and presently is widely used as a clinical marker for a number of hematologic malignancies (for review, see Horie and Watanabe, *Immunol* 10:457-470 (1998)). A naturally-occurring soluble form of the CD30 protein is found in human serum, and levels of this protein are elevated in a variety of pathological conditions including viral infection, allergic and autoimmune conditions and neoplastic diseases.

CD30 and CD30L are expressed on T cells, and appear to be involved in regulation of the immune system. Their expression on T cells is activation-dependent. CD30 has been reported to be a specific marker of $T_H2$ type T cells (Romagnani, *J Leukocyte Biol* 57:726 (1995); Romagnani, *J Clin Immunol* 15:121-129 (1995)). The $T_H2$ and $T_H2$ subsets of CD4$^+$ T cells can be distinguished based on which cytokines they predominantly express. Though individual T cells may actually secrete mixtures of these two groups of cytokines, chronic immune reactions are often dominated by one type or the other of CD4$^+$ T cells. T cells that produce $T_H2$ cytokines, which include IL-4, generally are considered to be mediators of allergic reactions. It has been suggested that the detection of circulating CD30$^+$ T cells could serve as a marker for $T_H2$-dominated allergic conditions such as atopic dermatitis (Yamamoto et al., *Allergy* 55:1011-18 (2000)); however, the correlation between CD30 expression and $T_H2$ phenotype has not held up over time (see, for example, Bengtsson et al, *J Leukocyte Biol* 58:683 (1996); Hamann et al., *J Immunol* 156:1387-91 (1996)). Based on experiments using a mouse model of diabetes, it has been proposed also that CD30-mediated signaling may protect against autoimmune disease (Kurts et al., *Nature* 398:341-344 (1999)). Others have reported that IL-4 upregulates, whereas IFNγ downregulates, the expression of CD30 on activated T cells (Nakamura et al., *J Immunol* 158:2090-98 (1997); Gilfillan et al., *J Immunol* 160:2180-87 (1998)).

The naturally-occurring ligand for CD30, CD30L, is a type II membrane glycoprotein that binds specifically with CD30, thus triggering CD30 to transmit a signal via its cytoplasmic domain. The isolation of mouse and human cDNAs encoding CD30L is described in U.S. Pat. No. 5,480,981. In addition to being expressed on activated T cells, CD30L is expressed on monocytes/macrophages, granulocytes and a subset of B cells (see, for example, U.S. Pat. No. 5,480,981). CD30L has been reported to induce murine B cell differentiation and the proliferation of activated T cells in the presence of an anti-CD3 co-stimulus (see, for example, Smith et al., *Cell* 73:1349-1360 (1993)). Moreover, it has been reported that CD30L exhibits "reverse signaling," that is, the cell surface CD30L that is expressed on neutrophils and peripheral blood T cells can be activated by cross-linking to stimulate metabolic activities in those cells (Wiley et al., *J Immunol* 157: 3235-39 (1996)).

There is a need to better understand the biological activities of CD30 and CD30L, and to exploit this knowledge in the treatment of human disease.

SUMMARY OF THE INVENTION

In accord with this invention, an agent capable of inhibiting the binding of CD30 to CD30L is used for treating an autoimmune or chronic inflammatory condition, the method comprising administering the agent to the patient according to a regimen of dose and frequency of administration that is adequate to induce a sustained improvement in at least one indicator that reflects the severity of the patient's condition. The improvement is considered to be sustained if the patient exhibits the improvement on at least two occasions separated by at least one day. The agent may be formulated into a physiologically acceptable pharmaceutical preparation, which may be packaged with a written matter describing the foregoing use. Moreover, an inhibitor of the CD30/CD30L interaction according to this invention may be administered concurrently with other treatments being used to treat the same disorder. In a preferred embodiment, the patient is a human.

In one of the embodiments of the invention, preferred agents for use in treating an autoimmune or inflammatory condition include an antibody that is specific for CD30L, a non-agonistic antibody that is specific for CD30, and a soluble CD30 polypeptide that comprises all or part of the extracellular region of human CD30. The nucleotide and amino acid sequences of human CD30 are shown in SEQ ID NO:6. Suitable CD30 polypeptides for use as therapeutic agents include proteins that comprise amino acids 19-390 of SEQ ID NO:6, or a fragment thereof that retains the ability to bind CD30L, including polypeptides having an at least 80%, at least 85%, at least 90%, at least 95%, at least 97.5%, or at least 99%, and most preferably at least 99.5% sequence identity with amino acids 19-390 of SEQ ID NO:6. Such polypeptides if administered in vivo are expected to bind with endogenous CD30L thereby interfering with the interaction between endogenous CD30 and endogenous CD30L. Such polypeptides may if desired be conjugated with another moiety, usually another protein, that promotes oligomerization. A moiety suitable for this purpose is the Fc region from an immunoglobulin molecule. Agents that antagonize the CD30/CD30L interaction may be used to prepare a pharmaceutical preparation to be administered in accord with the methods of the invention, either alone or concurrently with other treatments. Such pharmaceutical preparations may be packaged with a written matter describing the aforedescribed uses.

The hereindescribed therapeutic agents that inhibit the CD30/CD30L interaction may be used to treat a variety of diseases, including various arthritic conditions. For example, rheumatoid arthritis may be treated with the CD30/CD30L antagonists that are described above.

In one aspect of the invention, an agent capable of inhibiting the interaction of CD30 and CD30L is used concurrently with a second agent that is capable of antagonizing TNFα, IL-1α, IL-1β or IL-4. Medical disorders expected to be especially responsive to these combination treatments include multiple sclerosis, systemic sclerosis, acute inflammatory demyelinating polyneuropathy, acute motor axonal neuropathy, acute motor sensory axonal neuropathy, Fisher syndrome and systemic lupus erythematosus. As an example, the foregoing medical disorders may be treated with an antibody specific for CD30L used together with an antagonist of IL-4. The anti-CD30L antibody and the IL-4 antagonist are used for formulating pharmaceutical preparations for this purpose, and may be packaged separately or together in one package with a written matter describing this use. Suitable IL-4 antagonists for use in this method of treatment include but are not limited to an antibody specific for IL-4, an antibody specific for IL-4R and a soluble IL-4 receptor comprising amino acids 1-207 or 2-207 of SEQ ID NO:16. In one of the preferred embodiments of the invention, a patient who is suffering from systemic lupus erythematosus, scleroderma or pemphigus vulgaris is treated concurrently with an inhibitor of the CD30/CD30L interaction and an antibody specific for IL-4, an antibody specific for IL-4R or a soluble IL-4 receptor, wherein the receptor comprises amino acids 1-207 or amino acids 2-207 of SEQ ID NO:16.

In other aspects of the invention, provided are compounds, pharmaceutical preparations and methods of treatment for treating an autoimmune or chronic inflammatory condition that is resistant to treatment with an inhibitor of TNFα. This method comprises administering to a patient in need thereof an agent that is capable of inhibiting the binding of CD30 to CD30L or the binding of IL-1α or IL-1β to IL-R1, thereby blocking signal transduction by CD30 or IL-1. The agent is administered according to a regimen of dose and frequency of administration that is adequate to induce a sustained improvement in at least one indicator that reflects the severity of the patient's condition, the improvement being considered sustained if the patient exhibits the improvement on at least two occasions separated by at least one day. Agents suitable for use in such methods include an antibody that is specific for CD30, CD30L, IL-1α, IL-1β or IL-1R1, wherein the antibody may be a polyclonal antibody, a monoclonal antibody, a humanized antibody or a human antibody. Agents to be used for this purpose may be formulated into pharmaceutical preparations, which may be packaged with a written matter describing such use. One exemplary agent for this purpose is a soluble fragment of IL-1R2 that includes amino acids 1-333 of SEQ ID NO:8, or a subportion thereof that is capable of binding with IL-1α or IL-1β, thereby blocking signal transduction by IL-1α or IL-1β. Another agent suitable for treating such diseases is a soluble CD30 polypeptide that binds CD30L, such as a polypeptide comprising amino acids 19-390 of SEQ ID NO:6 or a CD30L-binding fragment thereof.

In yet another aspect of the invention, provided also is an animal model for screening therapeutic agents, the animal model being characterized by carrying genetic modifications that inactivate its p55 and p75 TNFα receptor proteins, and also by being genetically susceptible to experimentally-induced arthritis. In a preferred embodiment, the animal model is genetically susceptible is collagen-induced arthritis. For example, inactivation of the p55 and p75 TNFα proteins can be introduced into wild-type DBA/1, BUB or B10.Q mice or into DA, BB-DR or LEW rats, all of which are susceptible to collagen-induced arthritis. In a preferred embodiment, the animal is a DBA/1 mouse that has been genetically modified so that it has double-null mutations in both its p55 and p75 TNFα receptor genes.

The invention also provides methods for using the aforedescribed animal model to screen a candidate therapeutic agent to determine its efficacy in treating an autoimmune or chronic inflammatory condition that is resistant to treatment with a TNFα inhibitor. This method comprises assays in which one induces arthritis in an animal in which the p55 and p75 TNF receptors have been inactivated, administers the candidate therapeutic agent to the animal, and determines that the agent is efficacious if the severity of the animal's arthritis is reduced after the candidate agent has been administered. In a preferred embodiment, the screening assays employ a strain of mouse or rat that is susceptible to collagen-induced arthritis and in which the p55 and p75 proteins have been inactivated by genetic modification. In such mice, arthritis is induced by injecting collagen, the candidate therapeutic agent is administered, and then the severity of the arthritis is assessed by observing the amount of erythema and edema in the animals paws. In a preferred embodiment, the screening assays employ a DBA/1 mouse, a BUB mouse, a B10.Q mouse, a DA rat, a BB-DR rat or a LEW rat. A particularly suitable animal for use in these assays is a DBA/1 mouse carrying double-null mutations in its p55 and p75 TNFα receptor genes.

DETAILED DESCRIPTION OF THE INVENTION

The instant invention discloses methods and compounds for treating or preventing autoimmune and chronic inflammatory diseases, including conditions resistant to treatment with TNFα inhibitors, as well as a model system for screening agents for their efficacy in treating autoimmune or inflammatory conditions that are refractory to treatment with TNFα inhibitors. Patients treated in accord with the invention include those whose condition is continuous or intermittent. Diseases treatable by the subject methods include, for example, diseases such as arthritis, systemic lupus erythematosus and degenerative conditions of the nervous system, such as multiple sclerosis.

Preferably, the patient undergoing treatment is a mammal, and more preferably is a human. The subject methods are applicable to domestic animals, including pets and farm animals. Provided also herein are methods for using inhibitors that block CD30 or IL-1 signal transduction to treat autoimmune or chronic inflammatory diseases that are resistant to treatment with inhibitors of TNFα. In addition, methods are provided that involve treating the autoimmune or chronic inflammatory diseases described herein concurrently with two or more inhibitors selected from an IL-4 inhibitor, a TNFα inhibitor and an inhibitor of the CD30/CD30L interaction. For purposes of this disclosure, the terms "illness," "disease," "medical condition," "abnormal condition," "malady," "medical disorder", "disorder" and the like are used interchangeably.

Autoimmune conditions are characterized by the production of antibodies or effector T cells that react with native host molecules. Most B cell responses depend on helper T cells, thus the presence of autoantibodies generally involves some dysregulation of T cell function. In some cases, however, autoantibodies arise from normal T and B cell responses to foreign proteins that share antigenic epitopes with the host's own tissues. For example, autoantibodies may be elicited by a pathogenic bacteria that expresses an antigen that resembles a host molecule. In some instances, arthritic syndromes may originate in a woman due to her exposure to fetal cells that have escaped into her circulation during pregnancy. The phrase "chronic inflammatory condition" as used herein refers to chronic disorders whose ongoing symptoms do not appear to be caused by a viral or bacterial infection, even though these diseases in some instances may have been triggered by an infection that no longer is present. Such diseases are "inflammatory" in that they are characterized by the release of inflammatory cytokines such as tumor necrosis factor (TNFα), lymphotoxin α and/or interleukin-1 (IL-1), and they may also involve autoimmunity. In some cases, genetic predispositions play a role in autoimmune or chronic inflammatory diseases that are treatable by the subject methods. For such patients, the subject therapies may be administered prophylactically if desired.

In one aspect of the invention, autoimmune and chronic inflammatory diseases are treated by administering an agent that inhibits signal transduction by CD30. An agent's ability to inhibit CD30 signal transduction can be demonstrated using a biological assay, such as an assay that involves determining that the agent interferes with a biological activity manifested by $CD30^+$ cells that otherwise would occur when the cells are contacted with CD30L. Alternatively, a CD30 antagonist may be identified by determining its ability to prevent CD30L from binding CD30 that is expressed on the surface of cultured cells. Therapeutic agents of the invention include but are not limited to agents that antagonize the specific binding of CD30 to CD30L. The terms "antagonist" and "inhibitor" are used interchangeably herein.

The term "CD30-ligand" (CD30L) refers to a human or murine CD30-binding protein as disclosed in Smith et al. (1993) and U.S. Pat. No. 5,480,981, including CD30-binding muteins thereof. Nucleotide and amino acid sequences for human CD30L are shown in SEQ ID NOS:1 and 2, and those for mouse CD30L are shown in SEQ ID NOS:3 and 4. The extracellular region of human CD30L corresponds to amino acids 1-215 of SEQ ID NO:2. For forming soluble human CD30L molecules that can bind CD30, polypeptides comprising amino acids 44, 45, 46 or 47 through amino acid 215 of SEQ ID NO:2 may be used. The extracellular region of murine CD30L corresponds to amino acids 1-220 of SEQ ID NO:4. For forming soluble murine CD30L molecules that can bind CD30, polypeptides comprising amino acids 49-220 of SEQ ID NO:4 may be used.

As used herein, the phrase "fragment of CD30L" refers to a portion of a full-length CD30L polypeptide that retains the ability to bind to CD30, or that is capable of eliciting an antibody that binds specifically with a CD30L polypeptide of SEQ ID NO:2 or 4 or a subportion thereof. Such fragments preferably will contain at least a portion of the extracellular region of CD30L.

The term "CD30" as used herein refers to the 595 amino acid human CD30 polypeptide encoded by the nucleotide sequence of SEQ ID NO:5, and whose amino acid sequence is shown in SEQ ID NO:6. The cloning of CD30 is described in Durkop et al. (*Cell* 68:421 (1992)). The extracellular portion of human CD30 corresponds to amino acids 1-390 of SEQ ID NO:6, or if the signal peptide is removed, to amino acids 19-390 of SEQ ID NO:6. The phrase "soluble CD30" (sCD30) refers to soluble molecules that comprise all or part of the extracellular domain of the CD30 protein, and that retain the capacity to bind specifically with CD30L. Soluble CD30 polypeptides of the invention encompass recombinant sCD30 and naturally-occurring sCD30 proteins in highly purified form. If desired, the sCD30 may be linked to polyethylene glycol (i.e., pegylated) to prolong its half-life in the patient's body, or may be linked to another protein moiety that promotes oligomerization.

As used herein, the phrase "fragment of CD30" refers to a portion of a full-length CD30 polypeptide that retains the ability to bind to CD30L, or that is capable of eliciting an antibody that binds specifically with a CD30 polypeptide having the amino acid sequence SEQ ID NO:6 or subportion thereof or to a portion of full-length CD30 that is capable of transmitting a biological signal such as activation of NF-κB.

Soluble CD30 polypeptides according to the invention also include polypeptides that are at least 60%, or at least 70%, or at least 80%, and most preferably at least 90% of the length of the extracellular region of the human CD30 molecule. as shown in amino acids 1-390 of SEQ ID NO:6. Further included as therapeutic agents are proteins comprising a soluble CD30 polypeptide having at least 80%, at least 85%, at least 90%, at least 95%, at least 97.5%, or at least 99%, and most preferably at least 99.5% sequence identity with amino acids 1-390 of SEQ ID NO:6, where sequence identity is determined by comparing the amino acid sequences of the two polypeptides when aligned so as to maximize overlap and identity while minimizing sequence gaps. The value for percent identity in such comparisons can be determined by visual inspection and mathematical calculation. Alternatively, the percent identity of two amino acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters to be used for the GAP program in making these comparisons include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Polypeptide Sequence and Structure*, National Biomedical Research Foundation, pp. 353-358, 1979; (2) a penalty of 3.0 for each gap and an additional 0.10 penalty for each symbol in each gap; and (3) no penalty for end gaps. Other programs used by those skilled in the art of sequence comparison may also be used, such as, for example, the BLASTN program version 2.0.9, available for use via the National Library of Medicine website, or the UW-BLAST 2.0 algorithm, using standard default parameter settings described at the blast-wustl website. In addition, the BLAST algorithm uses the BLOSUM62 amino acid scoring matrix, and optional parameters that may be used are as follows: (A) inclusion of a filter to mask segments of the query sequence that have low compositional complexity (as determined by the SEG program of Wootton & Federhen (Computers and Chemistry, 1993); also see Wootton J C and Federhen S, 1996, Analysis of compositionally biased regions in sequence databases, *Methods Enzymol.* 266: 554-71) or segments consisting of short-periodicity internal repeats (as determined by the XNU program of Claverie & States (Computers and Chemistry, 1993)), and (B) a statistical significance threshold for reporting matches against database sequences, or E-score (the expected probability of matches being found merely by chance, according to the stochastic model of Karlin and Altschul (1990); if the statistical significance ascribed to a match is greater than this E-score threshold, the match will not be reported.); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

The phrase "CD30/CD30L interaction" as used herein refers to the specific binding of CD30 to CD30L, resulting in signal transduction by CD30. This includes instances in which at least one binding partner is a fragment of either CD30 or CD30L, that is, the term may refer to the binding interaction of a CD30 fragment to CD30L, CD30 to a CD30L fragment, or a CD30 fragment to a CD30L fragment. In addition, a CD30/CD30L interaction can involve an analog of CD30 (such as an allelic variant or mutein) that is capable of binding specifically to CD30L, or may involve an analog of CD30L (such as an allelic variant or mutein) that can bind specifically with CD30. Moreover, a CD30/CD30L interaction can involve either endogenous CD30 or CD30L proteins or may involve recombinant CD30 or CD30L expressed by a cell transfected with a nucleic acid encoding the recombinant protein. Similarly, the phrase "IL-1/IL-1R interaction" refers to the specific binding between IL-1 and IL-1R, including instances where at least one of the binding partners is a fragment of the full-length polypeptide, and including instances where one of the binding partners is an allelic variant or mutein that retains the ability to bind specifically with its binding partner.

The term "IL-1" as used herein includes both IL-1α and IL-1β. IL-1α and IL-1β are two distinct proteins that both are instrumental in inflammation, and both of which bind the same two cell surface receptors. The cell surface receptors to which IL-1α and IL-1β both bind are known as types I and II IL-1 receptors, or "IL-1R1" and "IL-1R2." Signal transduction by IL-1 is mediated primarily by IL-1R1, while IL-1R2 is considered to be a "decoy" receptor whose function is to downregulate IL-1 biological activity. Human IL-1R2 is described in U.S. Pat. No. 5,350,683. A nucleic acid sequence encoding the IL-1R2 protein is shown in SEQ ID NO:7, and the amino acid sequence is shown in SEQ ID NO:8.

In one embodiment, the subject invention provides methods of treating autoimmune or chronic inflammatory conditions that are resistant to treatment with drugs that inhibit TNFα. In such patients, the lack of response to TNFα inhibition may be partial or complete. TNFα inhibitors to which these diseases are unresponsive may include one or more of the following: etanercept (p75 TNFR:Fc, sold as ENBREL®; Immunex Corporation); LENERCEPT® (p55 TNFR-Ig fusion protein; Roche); or antibodies against TNFα, including humanized antibodies such as infliximab (REMICADE®; Centocor), D2E7 (BASF Pharma) or CDP571 (HUMICADE®; Celltech). Arthritis that is resistant to one of these or to another TNF inhibitor is referred to as "TNFα-independent arthritis." Diseases resistant to treatment with TNFα inhibitors may be treated by administering one or more agents that inhibit signal transduction by CD30 or IL-1, such as an inhibitor of the CD30/CD30L interaction and/or of the IL-1/IL-1R interaction. In addition, diseases that are less than fully responsive to TNFα inhibitors are treated with a combination of a TNFα inhibitor administered concurrently with an inhibitor of the CD30/CD30L interaction and/or with an inhibitor of an IL-1/IL-1R interaction.

Therapeutic Agents

Any physiologically acceptable agent capable of blocking signal transduction by CD30 may be used as a therapeutic agent in the disclosed methods of treatment, including but not limited to: antibodies that bind specifically to CD30L and thereby inhibit its binding to CD30; non-agonistic antibodies that bind specifically to CD30 and inhibit its ability to transmit a biological signal; muteins or analogs such as allelic variants of CD30L or fragments thereof that bind to CD30 but that do not stimulate transduction of a biological signal; sCD30 molecules that contain the extracellular domain of CD30 or a portion thereof that is capable of binding CD30L; and small organic molecules that block signal transduction by CD30 or that interfere with the biological functioning of CD30L.

Soluble CD30 molecules used as therapeutic agents as described herein comprise the extracellular region of CD30. An exemplary CD30 protein is shwon in SEQ ID NO:6, in which amino acids 1-390 of SEQ ID NO:6 correspond to the extracellular region. If less than the entire extracellular domain is used, the fragment must retain the ability to bind CD30L, which ability may be ascertained using any convenient binding assay format. The presence of the signal peptide in the sCD30 is optional. Suitable assays include testing for the ability of the sCD30 to competitively block binding of labeled CD30L to cells expressing surface CD30 or to block binding of isolated CD30L or cells expressing surface CD30L to cell-surface CD30 or CD30 that is anchored to a solid support such as an ELISA plate or a chromatography matrix, such as agarose beads. When used therapeutically, these sCD30s block the binding of membrane-bound CD30 to cells expressing CD30L sCD30s useful as CD30 antagonists for the disclosed therapeutic methods include oligomeric sCD30 polypeptides (such as dimers or trimers), as well as monomers. Oligomers may be linked by disulfide bonds formed between cysteine residues on different sCD30 polypeptides. In one embodiment of the invention, the therapeutic agent is a sCD30 that is created by fusing the extracellular domain of CD30 (or a CD30L binding portion thereof) to the Fc region of an antibody, preferably a human antibody, in a manner that does not interfere with binding of the CD30 moiety to CD30L. The resulting fusion protein is a CD30:Fc that will dimerize by the spontaneous formation of disulfide bonds between the Fc moieties on two of the fusion protein chains. Native Fc region polypeptides or muteins thereof may be employed in making these constructs. Suitable CD30:Fc's will reduce or abolish the ability of agonistic anti-CD30 antibodies to stimulate CD30, or will competitively inhibit the binding of CD30L to membrane-bound CD30. An example of a suitable CD30:Fc protein that may be used in the subject methods is one that is constructed as described in U.S. Pat. No. 5,677,430.

Other suitable oligomeric sCD30 polypeptides may be prepared by fusing the extracellular domain of CD30 (or a fragment thereof) to a "leucine zipper," which is a peptide that promotes oligomerization of the proteins in which they are present. Leucine zippers are motifs found in several DNA-binding proteins (see, for example, Landschulz et al., *Science* 240:1759 (1988)), and naturally-occurring leucine zipper peptides and derivatives thereof can promote the formation of dimers or trimers of protein chains in which they are present. Examples of leucine zipper domains useful for producing soluble oligomeric proteins are described in WO 94/10308.

Another method of linking multiple copies of soluble CD30 polypeptides is by fusing monomers together with suitable peptide linkers. A fusion protein comprising two or more copies of sCD30 separated by peptide linkers may be produced by recombinant DNA technology. Such peptide linkers optimally are from 5 to 100 amino acids in length, preferably comprising amino acids selected from the group consisting of glycine, asparagine, serine, threonine, and alanine. The production of recombinant fusion proteins comprising peptide linkers is illustrated in U.S. Pat. No. 5,073,627.

In yet other embodiments, antagonists can be designed to reduce the level of endogenous CD30 or CD30L gene expression, for example, by using well-known antisense or ribozyme approaches to inhibit or prevent translation of CD30 or CD30L mRNAs; triple helix approaches to inhibit transcription of CD30 or CD30L genes; or targeted homologous recombination to inactivate or "knock out" the CD30 or CD30L genes or their endogenous promoters or enhancer elements. Such antisense, ribozyme, and triple helix antagonists may be designed to reduce or inhibit either unimpaired, or if appropriate, mutant CD30 or CD30L gene activity. Techniques for the production and use of such molecules are well known to those of skill in the art.

Antisense RNA and DNA molecules can act to directly block the translation of mRNA by hybridizing to targeted endogenous mRNA thereby preventing translation. Alternatively, antisense RNA or DNA can inhibit or prevent transcription of the target gene. The antisense approach involves designing oligonucleotides (either DNA or RNA) that are complementary to a CD30 or CD30L mRNA, or complementary to a portion of the target gene, such as a regulatory element that controls transcription of the gene. Antisense nucleic acids should be at least six nucleotides in length, and are preferably oligonucleotides ranging from 6 to about 50 nucleotides in length.

In one embodiment of the invention, ribozyme molecules designed to catalytically cleave CD30 or CD30L mRNA transcripts are used to prevent translation of CD30 or CD30L mRNA and expression of CD30 or CD30L polypeptides. (See, e.g., WO 90/11364, or U.S. Pat. No.5,824,519).

Provided herein are therapies for treating autoimmune and chronic inflammatory conditions that are resistant to treatment with an inhibitor of TNFα. Therapies according to this embodiment of the invention are administered to a patient who has already been observed to be partially or fully unresponsive to treatment with a TNFα inhibitor. To treat a patient whose autoimmune or chronic inflammatory condition is resistant to a TNFα inhibitor, the patient is administered an effective amount of an agent that is capable of blocking the binding of CD30 to CD30L, such as one of the inhibitors described above. Alternatively, the patient is administered an IL-1 antagonist that is capable of inhibiting signal transduction by IL-1, such as by reducing the amount of IL-1 produced in the patient's body, or by interfering with the binding of IL-1 to IL-1R1. In the case of patients who are partially responsive to treatment with a TNFα inhibitor, treatments according to this embodiment of the invention may be administered concomitantly with a TNFα inhibitor. The therapeutic agents of this embodiment of the invention generally are administered in the form of a physiologically acceptable composition.

In a further embodiment of the invention, patients are treated with an inhibitor of the CD30/CD30L interaction administered concurrently with an antagonist of IL-4. IL-4 is a cytokine with a broad range of activities, and is expressed by CD30+ T cells. The cell surface receptors to which IL-4 binds are referred to as the "IL-4 receptor" or "IL-4R." (see for example, U.S. Pat. No. 5,599,905). The interaction between IL-4 and its receptor can be inhibited by administering a soluble IL-4 receptor (sIL-4R), such as the sIL-4Rs described in U.S. Pat. No. 5,599,905. Preventing this interaction will hinder or prevent IL-4-mediated biological activities. IL-4 can induce a chronic inflammatory effect in some diseases and can exacerbate some autoimmune disorders. In such diseases, the infiltration and proliferation of $T_H2$ cells is fueled by IL-4 and CD30 signal transduction. These cells cause the overproduction of IL-4. Accordingly, diseases where this occurs, including atopic dermatitis, asthma, systemic lupus erythematosus, scleroderma or pemphigus vulgaris, are effectively treated by administering an agent that inhibits IL-4 concurrently with an agent that inhibits the interaction between CD30 and CD30L. The latter preferably is an antibody that is specific for CD30L.

Methods of using IL-4 inhibitors to treat immune or inflammatory responses are illustrated, for example, in U.S. Pat. No. 5,767,065. IL-4 antagonists that may be administered in combination with inhibitors of the CD30/CD3-L interaction include, but are not limited to, IL-4 receptors (IL-4R) and other IL-4-binding molecules, IL-4 muteins and antibodies that bind specifically with IL-4 or IL-4 receptors thereby blocking signal transduction, as well as antisense oligonucleotides and ribozymes targeted to IL-4 or IL-4R. Polyclonal or monoclonal antibodies specific for IL-4 or IL-4 receptor may be prepared using standard procedures. Among the IL-4 receptors suitable for use as described herein are soluble fragments of human IL-4R that retain the ability to bind IL-4. Such fragments retain all or part of the IL-4R extracellular region and are capable of binding IL-4. In a preferred embodiment of the invention, the patient is treated concurrently with sIL-4R and an antibody specifically for CD30L.

IL-4 receptors are described in U.S. Pat. No. 5,599,905; Idzerda et al., *J. Exp. Med.* 171:861-873, March 1990 (human IL-4R); and Mosley et al., *Cell* 59:335-348, 1989 (murine IL-4R), each of which is hereby incorporated by reference in its entirety. The protein described in those three references is sometimes referred to in the scientific literature as IL-4Rα. Unless otherwise specified, the terms "IL-4R" and "IL-4 receptor" as used herein encompass this protein in various forms that are capable of functioning as IL-4 antagonists, including but not limited to soluble fragments, fusion proteins, oligomers, and variants that are capable of binding IL-4. Suitable IL-4Rs include variants in which valine replaces isoleucine at position 50 (see Idzerda et al., 1990), and include slow-release formulations, and PEGylated derivatives (modified with polyethylene glycol) are contemplated, as well as recombinant fusion proteins comprising heterologous polypeptides fused to the N-terminus or C-terminus of an IL-4R polypeptide, including signal peptides, immunoglobulin Fc regions, poly-His tags or the FLAG® polypeptide described in Hopp et al., *Bio/Technology* 6:1204, 1988, and U.S. Pat. No. 5,011,912, as well as fusions of IL-4 receptors with oligomer-promoting leucine zipper moieties. Soluble recombinant fusion proteins comprising an IL-4R and immunoglobulin constant regions are described, for example, in EP 464,533. A nucleotide sequence encoding human IL-4 receptor is shown in SEQ ID NO:15 and amino acid sequence for human IL-4 receptor is shown in SEQ ID NO:16. In a preferred embodiment, the IL-4 antagonist to be used in combination with an inhibitor of the CD30/CD30L interaction is a soluble human IL-4 receptor comprising amino acids 1 to 207 of SEQ ID NO:16 and in another preferred embodiment, the IL-4 antagonist comprises amino acids 2 to 207 of SEQ ID NO:16. IL-4 antagonists useful for the hereindescribed methods of treatment also include molecules that selectively block the synthesis of endogenous IL-4 or IL-4R, such as antisense nucleic acids or ribozymes targeted against either of these molecules.

Various IL-4 antagonists that may be used for the herein described methods of treatment can be identified, for example, by their ability to inhibit $^3$H-thymidine incorporation in cells that normally proliferate in response to IL-4, or by their ability to inhibit binding of IL-4 to cells that express IL-4R. In one assay for detecting IL-4 antagonists, one measures the ability of a putative antagonist to block the IL-4-induced enhancement of the expression of CD23 on the surfaces of human B cells. For example, B cells isolated from human peripheral blood are incubated in microtiter wells in the presence of IL-4 and the putative antagonist. Following the incubation, washed cells are then incubated with labelled monoclonal antibody against CD23 (available from Pharmingen) to determine the level of CD23 expression. An anti-huIL-4R murine mAb (R&D Systems) previously shown to block the binding and function of both hIL-4 and hIL-13 may used as a positive control for neutralization of CD23 induction by IL-4. Alternatively, suitable IL-4 antagonists may be identified by determining their ability to prevent or reduce the impaired the barrier function of epithelium that results when IL-4 is incubated with the epithelium. For this purpose, one may use confluent monolayers of human epithelial cell lines such as Calu-3 (lung) or T84 (intestinal epithelium). Incubation of such monolayers with IL-4 causes significant damage to their barrier function within about 48 hours. To assay IL-4 antagonists, monolayers may be tested for their permeability, for example, by adding radiolabeled mannitol to cells incubated with IL-4 in the presence or absence of an antagonist. Alternatively, transepithelial resistance (indicating an intact barrier) may be determined using a voltmeter.

In other embodiments of the invention, antagonists of the CD30/CD30L interaction are administered concurrently with an IL-1 antagonist. Alternatively, IL-1 antagonists may be administered alone for treating autoimmune or inflammatory conditions that are resistant to treatment with TNFα inhibitors. Suitable agents for inhibiting signal transduction by IL-1 include antibodies specific for IL-1 or IL-1R1, particularly humanized antibodies. Other suitable IL-1 antagonists include: IL-1 receptor antagonist (IL-1ra); receptor-binding fragments of IL-1 that block native IL-1 from binding IL-1R1; antibodies directed against IL-1 or IL-1R1; and recombinant proteins comprising all or part of a receptor for IL-1 or modified variants thereof, including genetically-modified muteins, multimeric forms and sustained-release formulations. IL-1ra is a naturally-occurring endogenous antagonist of IL-1 and binds both IL-1R1 and IL-1Rs. Preferred IL-1 antagonists include soluble IL-1R2 molecules that are capable of binding IL-1 and that comprise all or part of the extracellular domain of IL-1R2. These soluble IL-1R2 molecules block IL-1 from interacting with membrane-bound IL-1R1. Other useful IL-1 antagonists include soluble forms of IL-1R1 that are capable of competitively inhibiting the interaction of IL-1 with IL-1R1 and further include IL-1β converting enzyme (ICE) inhibitors, which generally are small organic molecules. A preferred IL-1 antagonist is a soluble fragment of IL-1R2 that includes amino acids 1-333 of SEQ ID NO:8, or a subportion thereof that is capable of binding specifically with IL-1α or IL-1β. Soluble IL-1R2s to be used in accord with the invention include, for example, analogs or fragments of native IL-1R2 having at least 20 amino acids, that lack the transmembrane region of the native molecule, and that are capable of binding IL-1. The ability of soluble IL-1R2 to bind IL-1 (including binding to fragments of IL-1α or IL-1β) can be assayed using ELISA or any other convenient assay.

Other suitable IL-1 antagonists are chimeric proteins in which one of the IL-1 antagonists described above is fused with another polypeptide that promotes the spontaneous formation of a dimer, trimer or higher order multimer. A suitable polypeptide moiety for promoting dimerization is the Fc region of a human immunoglobulin. For example, soluble IL-1R2 polypeptides or fragments thereof may be fused the Fc region of an immunoglobulin to form a chimeric protein that is capable of dimerizing. Any of the foregoing IL-1 antagonists, other than ICE inhibitors, may be covalently linked to polyethylene glycol (pegylated) to prolong their half-life in the body.

It is understood that while IL-1α and IL-1β are the IL-1s most commonly associated with inflammation, other forms of IL-1 exist, and the invention encompasses the use of therapeutic agents targeting these other forms for treating autoimmune and chronic inflammatory diseases that are resistant to treatment with TNFα inhibitors.

Preferred agents for use in the subject therapeutic methods include antibodies that block the CD30/CD30L, IL-1/IL-1R or IL-4/IL-4R interactions. Such antibodies are specifically immunoreactive with their target, that is, they bind to the target protein via the antigen-binding site of the antibodies and do not bind unrelated proteins to a significant degree. Antibodies specific for CD30L will bind endogenous CD30L, thus reducing the amount of endogenous CD30L available for binding to cell surface CD30. Also suitable for use as a therapeutic agent of the subject invention are biologically active fragments of antibodies. For example, a biologically active fragment of an anti-CD30L antibody is an antibody protein that is truncated relative to the intact antibody, but that retains the ability to specifically bind CD30L and to block its interaction with CD30. Antigen-binding fragments of antibodies, include, but are not limited to, Fab and F(ab')$_2$ fragments, and may be produced by conventional procedures.

Antibodies that antagonize the CD30, IL-1 or IL-4 signal transduction can be identified in any suitable assay, including assays based on biological function or assays based on the detection of physical binding. Examples of such assays are disclosed, for example, in U.S. Pat. No. 5,677,430. One preferred assay tests an antibody's ability to block the binding of cell surface CD30L to cell surface CD30. Cell lines suitable for such assays include the CD30+ HDLM-2 or L540 cell lines, or may use activated T cells expressing CD30. An assay based on biological function, for example, could entail determining whether an antibody can antagonize the ability of membrane-bound CD30L to stimulate proliferation of CD30$^+$ cells that are responsive to such stimulation. Yet another assay employs the CD30$^+$ K299 human cell line. It has been observed that proliferation of these cells is inhibited by contact with CD30L-transfected cells. An antibody specific for CD30L (or other antagonist that blocks CD30L) could suppress this effect of CD30L and thus enhance the proliferation of these cells in this assay. In other instances, the antibody is tested for its ability to block the binding of labeled recombinant CD30L to cell surface CD30. In other instances, the assays employ cells transfected with DNA encoding human CD30L, IL-1R1, IL-1R2 or IL-4R. For example, the ability of a monoclonal antibody against human CD30L to block CD30/CD30L interactions can be assessed by determining whether it can block the binding of human CD30:Fc to either cells transfected with human CD30L or to activated human T cell blasts as assessed by FACS analysis. Similarly, the specificity of an antibody for IL-4R could be tested by determining if the antibody blocks binding of labeled IL-4 to IL-4R.

Other suitable assays utilize soluble forms of both binding partners, for example, sCD30 and sCD30L. For example, sCD30 may be bound to a solid phase, such as a column chromatography matrix or to an ELISA plate. For an ELISA assay using sCD30 and sCD30L, a sCD30, such as CD30: Fc, is fixed to an ELISA plate, and an antibody raised against CD30L is tested to see if it is an antagonist by checking its ability to inhibit the binding of a soluble CD30L leucine zipper construct to the anchored sCD30. In this assay, binding of the leucine zipper construct or other soluble CD30L to the ELISA plate is measured using a biotinylated non-neutralizing anti-CD30L monoclonal antibody, or alternatively, by using an antibody to the leucine zipper end of the CD30L construct. Other assays test the ability of an antibody to block the binding of IL-1 to cell surface IL-1R1.

Therapeutic agents suitable for use in the subject methods include non-agonistic antibodies against human CD30. Such antibodies can block the CD30/CD30L interaction. Monoclonal antibodies against human CD30 can be prepared, for example, as described in U.S. Pat. No. 5,677,430, then tested to determine if they are agonistic or non-agonistic. A non-agonistic antibody against CD30 may be distinguished from an agonistic antibody by testing its effect on CD30 in a suitable biological assay, such as the assays described U.S. Pat. No. 5,677,430. In one such assay, an antibody specific for CD30 is tested to determine whether it can induce proliferation of activated T cells prepared from peripheral blood or whether it can induce proliferation of the Hodgkin's disease-derived cell lines HDLM-2 or L-540. An agonistic antibody, will induce such proliferation. In contrast, a non-agonistic antibody against CD30 will bind specifically with CD30 but will not induce proliferation of target cells in these or other assays that rely on signal transduction by CD30.

Therapeutic agents according to this invention may be administered concurrently with one or more additional therapeutic molecules to treat autoimmune or chronic inflammatory diseases. As used herein, "concurrently" includes instances where the drugs in a combination treatment are administered over the same time period or are alternated. This includes simultaneous and sequential administration, and the different drugs may be present in the same or separate pharmaceutical compositions. The frequency and route of administration for the different drugs in such combinations may be the same or different. Therapeutic agents that may be used in such combinations include, for example, antagonists of CD30, IL-1 or IL-4 as described above, and also include non-steroidal anti-inflammatory drugs (NSAIDs), corticosteroids, analgesics, cytokine suppressive drugs, disease-modifying anti-rheumatic drugs (DMARDs), methotrexate, and so on. As an example, antagonists of CD30 or IL-1 may be combined with each other or with antagonists of TNFα, IL-2, IL-6, RANK or other cytokines that may contribute to autoimmunity or chronic inflammation. In some preferred embodiments, the additional therapeutic agents target a cytokine. An antagonist that targets a cytokine may comprise a soluble receptor against the cytokine, and usually includes part or all of the extracellular domain of a receptor for the cytokine. The soluble cytokine receptor may be used as a monomer, or as a dimer or higher multimer (for example, as a fusion molecule wherein the soluble receptor is attached to the dimer-promoting Fc portion of human immunoglobulin). In other embodiments, the soluble cytokine receptor is pegylated to increase its serum half-life. In some embodiments, the soluble cytokine antagonist comprises a soluble TNF receptor (type I or II). Small organic molecules that inhibit inflammatory cytokines may also be used in combination with the subject therapeutic agents. More than one antagonist of CD30 signal transduction may be administered concurrently for treating autoimmune or chronic inflammatory diseases, and may be administered alone or together with other drugs that are effective against the same autoimmune or chronic inflammatory condition or that are being administered to treat a different condition in the same patient.

Combinations used to treat multiple sclerosis include inhibitors of CD30 administered in conjunction with other drugs used to treat this condition, including but not limited to mitoxantrone (NOVANTRONE®; Immunex Corporation), interferon β-1a (AVONEX®; Ares-Sorono Group), interferon β-1b (BETASERON®; Berlex Laboratories, Inc.) and/or glatiramer acetate (COPAXONE®; Teva Pharmaceuticals). IL-4 antagonists may be added to any of the foregoing combination.

For treating various rheumatic conditions, including rheumatoid arthritis, an agent capable of inhibiting CD30 signal transduction may be administered alone or concurrently with inhibitors of TNFα, such as antibodies against TNFα (for example, humanized antibodies such as REMICADE® (Centocor), D2E7 (BASF Pharma), or HUMICADE® (Celltech)); soluble forms of the TNF receptor (such as ENBREL® (Immunex Corporation) or LENERCEPT® (Roche) or pegylated soluble TNF receptors.

Preparation of Therapeutic Antibodies

CD30L polypeptides suitable for use as an immunogen in producing therapeutic anti-CD30L antibodies include but are not limited to full length CD30L (recombinant or prepared from a naturally-occurring source) or immunogenic fragments thereof, particularly fragments containing all or part of the extracellular domain of CD30L. To be effective as an immunogen, a fragment of CD30L need not retain the capacity to bind CD30, but must be large enough to be antigenic. To be antigenic, a peptide generally must contain at least 20 amino acids. The amino acid sequence of full-length human CD30L is shown in SEQ ID NO:2 and mouse CD30L in SEQ ID NO:4; peptides corresponding to at least 20 contiguous amino acids of either of these proteins may be used as an immunogen to prepare therapeutic agents for use as described herein.

CD30 polypeptides suitable for use as immunogens in producing non-agonistic anti-CD30 antibodies include but are not limited to full length CD30 proteins (recombinant or prepared from a naturally-occurring source) or immunogenic fragments thereof, particularly fragments comprising all or part of the extracellular domain as defined by amino acids 1-390 of SEQ ID NO:6. Immunogens for raising anti-CD30 antibodies preferably contain at least 20 contiguous amino acids of the protein shown in SEQ ID NO:6.

IL-1 or IL-1R polypeptides suitable for use as immunogens in producing antagonistic antibodies include but are not limited to full length proteins (recombinant or prepared from a naturally-occurring source) or immunogenic fragments thereof, particularly fragments comprising all or part of the extracellular domain of human IL-1R2 as shown in amino acids 1-333 of SEQ ID NO:8. Preferred immunogens contain at least 20 contiguous amino acids of the protein shown in SEQ ID NO:8.

Immunogens for raising therapeutic antibodies against TNFα, TNFR, IL-4 or IL4-R will consist of an at least 20 amino acid segment of the target protein. Suitable antigens for raising therapeutic antibodies also include any of the aforementioned immunogens fused to another protein, including proteins fused to an N-terminal "flag" (see, for example, Hopp et al., *Bio/Technology* 6:1204 (1988); U.S. Pat. No. 5,011,912), or fused to the Fc portion of an immunoglobulin molecule, preferably a human immunoglobulin. Preferred therapeutic agents include both polyclonal and monoclonal antibodies (MABs), either of which may be generated using the above-described polypeptides as immunogens.

Polyclonal antibodies may be generated according to standard protocols using a variety of warm-blooded animals such as horses, cows, rabbits, mice, rats, or various species of fowl. In general, the animal is immunized with CD30L, CD30, IL-1, IL-1R1, TNFα, TNFR1 or TNFR2, or an immunogen derived therefrom, through intraperitoneal, intramuscular, or subcutaneous injections. The immunogenicity of an immunogenic polypeptide usually is increased through the co-administration of an adjuvant such as RIBI® (Corixa), or Freund's complete or incomplete adjuvant, or other suitable adjuvant. After several booster immunizations, serum samples are collected and tested for specific reactivity with the target polypeptide by any suitable method, such as ELISA, antibody-capture ("ABC") or modified ABC assays, or a dot blot assay. Once the titer of antibody has reached a plateau in terms of reactivity to the target, the polyclonal antiserum is harvested.

For an ABC assay, a plastic dish, such as an ELISA plate, is coated with an antibody that is specifically reactive with the Fc portion of immunoglobulin from for the same species of animal that was used to raise the antibody against the target polypeptide. For example, if a target protein is was injected into a rabbit and the resulting anti-target polyclonal antibody is to be evaluated for specificity, the plates are coated with antibody specifically reactive with the Fc portion of rabbit IgG. In the next step, a sample of antibody from the immunized rabbit is incubated in the dish under conditions that promote binding between the rabbit IgG and the anchored anti-rabbit antibody. Next, labeled target protein is added, and the dish is incubated under conditions that promote antibody binding. If the sample of antibody being tested is specific for the target protein, then the labeled target protein will become bound to the captured rabbit antibody, and thereafter can be detected after the plate is washed. For example, if the target protein is labeled with biotin, target protein that has become bound can be detected by using a streptavidin-tagged enzyme that is capable of generating a colored product.

Suitable procedures for generating monoclonal antibodies include several methods described in the art (see, for example, U.S. Pat. No. 4,411,993; Kennett et al. (eds.), *Monoclonal Antibodies, Hybridomas: A New Dimension in Biological Analyses*, Plenum Press, New York (1980); and Harlow and Lane (eds.), *Antibodies: A Laboratory Manual*, Cold Spring Harbor Laboratory Press, Cold Spring Harbor, N.Y. (1988)). Mice or rats generally are used for the initial immunizations, which are performed as described above for raising polyclonals. After immunization, the immunized animal's spleen cells are harvested and fused according to standard procedures with a myeloma cell line to yield immortalized hybridoma cells that produce monoclonal antibodies. Many myeloma lines suitable for hybridomas are known, including many that are available from the American Type Culture Collection (ATCC), Rockville, Md. (see *Catalog of Cell Lines & Hybridomas*, ATCC). Individual hybridoma cells are isolated after the fusion step to be screened to identify those producing monoclonal antibodies having the desired specific immunoreactivity. For therapeutic use, high affinity antibodies are preferred. Hybridomas with the desired specification are identified by assays such as ELISA, ABC, modified ABC, or dot blot assays, then are isolated and propagated. The monoclonal antibodies are harvested and purified using standard methods.

Monoclonal antibodies against CD30L may be raised and screened for specific reactivity according to the methods described in U.S. Pat. No. 5,677,430 or by any of the various methods known in the art for raising monoclonals. Screening may involve determining the capacity of the monoclonals to antagonize the binding of cell-surface CD30L to cell-surface CD30 or to antagonize signal transduction by cell-surface CD30.

Antibodies useful for the subject therapeutic methods also include chimeric antibodies and antibodies produced or modified via protein engineering or recombinant DNA technology (see, for example, Alting-Mees et al., *Strategies in Molecular Biology* 3:1 (January, 1990)). Production of chimeric and otherwise engineered antibodies is described in the prior art (see, for example, Reichmann et al., *Nature* 332:323 (1988); Liu et al., *PNAS* 84:3439 (1987); Larrick et al., *Bio/Technology* 7:934 (1989); and Winter and Harris, *TIPS* 14:139 (1993)).

When an antibody is to be administered as a therapeutic agent to a human patient in accord with the subject methods, a humanized antibody is preferred. Even more preferred are human antibodies. Humanized antibodies comprise an antigen binding domain derived from a non-human antibody (for example, a rat or mouse), and may contain the entire variable region of the non-human antibody, or may contain only that portion of the non-human variable region that includes the antigen-binding site. In a preferred embodiment of the invention, the only non-human portion of the humanized antibody is the hypervariable region. Procedures for preparing humanized antibodies are known, and include techniques that involve recombinant DNA technology. Production of humanized antibodies is described, for example, in Winter and Harris, 1993. To create a humanized antibody, DNA encoding the antigen-binding sites of a monoclonal antibody directed against the target may be isolated and inserted directly into the genome of a cell that is producing human antibodies (see Reichmann et al. (1988)). For example, this method could be used for antibodies against CD30, CD30L, IL-1, IL-1R1, TNFα, TNFR-1 or TNRF-2, IL-4 or IL-4R.

In one procedure for preparing humanized antibodies, cDNA is prepared on a mRNA template derived from a hybridoma cell line that produces a non-human monoclonal antibody having the desired specificity. In essence, a fragment of the cDNA that encodes the variable region of the monoclonal antibody (or a fragment thereof containing the antigen binding site) is isolated, and this cDNA fragment is fused to DNA encoding the human counterpart of the remainder of the human antibody molecule, thereby reconstructing a functional antibody molecule. Host cells are transfected with an expression vector containing the fused gene, and are cultured to produce the desired recombinant fusion protein. To isolate DNA encoding the variable region of an immunoglobulin chain, one may employ, for example, the method of Larrick et al. (1989), which involves the polymerase chain reaction (PCR), using a mixture of upstream primers corresponding to the leader sequence, and a downstream primer based on the conserved sequence of the constant region. PCR primers for amplifying the variable region from mouse or human hybridoma cell immunoglobulin mRNA are commercially available (for example, from Stratacyte, La Jolla, Calif.). PCR primers may be used to amplify heavy or light chain variable region DNA, and the resulting amplified DNA may be inserted into vectors such as ImmunoZAP*H or ImmunoZAP*L (Stratacyte), respectively, for expression in E. coli.

To produce a humanized antibody for use as a therapeutic agent in accord with the invention, variable region DNA is isolated from a murine or rat hybridoma cell that expresses an antibody with the desired specificity, and this DNA is fused with a constant region DNA amplified from a cDNA encoding a human antibody. These or similar techniques may be used, for example, to produce a single-chain antigen-binding protein containing a $V_L$ domain fused to a $V_H$ domain through a peptide linker (see Bird et al., Science 242:423 (1988)). Further genetic manipulations may be performed to replace all but the hypervariable regions of the antibody with human sequences.

Human antibodies may be generated using methods involving non-human animals. For example, DNA encoding one or more entire human immunoglobulin chains may be introduced into a mouse to produce a transgenic animal, and then the antibody is isolated from cultured cells derived from the mice. The endogenous immunoglobulin genes in the recipient mouse may be inactivated by various means, and human immunoglobulin genes introduced into the mouse to replace the inactivated genes. These genetic manipulations will result in human immunoglobulin polypeptide chains replacing endogenous immunoglobulin chains in at least some instances, and in such mice some or most of the antibodies produced upon immunization will be human antibodies. Examples of techniques for the production and use of such transgenic animals are described in U.S. Pat. Nos. 5,814,318, 5,569,825, and 5,545,806.

Animal Model for Diseases Resistant to Treatment with TNFα Inhibitors

TNF inhibition has demonstrated beneficial effects in a significant percentage of rheumatoid arthritis patients and patients with other kinds of arthritis or other chronic inflammatory diseases. However, a subset of rheumatoid arthritis patients respond poorly or not at all to treatment with TNF inhibitors (TNF-independent rheumatoid arthritis). To provide a tool for identifying effective treatments for patients with autoimmune or chronic inflammatory conditions that show little or no improvement in response to treatment with TNFα inhibitors, provided herein is an animal model that is useful for screening candidate therapeutic agents that may be effective for such diseases. The model animal is characterized by carrying genetic modifications that inactivate its p55 and p75 TNFα receptor proteins and by being genetically susceptible to experimentally-induced arthritis. The animal model is created by genetically modifying a strain of animal that already is known to be genetically susceptible to experimentally-induced arthritis. Provided also are methods for screening candidate therapeutic agents to determine their effectiveness in treating a medical disorder that is resistant to treatment with a TNFα inhibitor. Such medical disorders include rheumatoid arthritis and other kinds of arthritis.

The subject animal model is created by introducing genetic modifications into a strain of animal, usually a mammal, that prior to modification is genetically susceptible to experimentally-induced arthritis. The genetic modifications result in the inactivation of the animal's p55 and p75 TNFα receptor (TNFR) proteins. The p55 and p75 TNFRs are also called the types I and II TNFRs, respectively.

A model animal according to the subject invention may be deficient in its p55 and p75 TNFR proteins as the result of any of several different types of mutation strategies. For example, the deficiency may result from mutations that inhibit the transcription of a translatable TNFR messenger RNA or that result in production of defective TNFR proteins that do not bind TNFα. Cells from the subject animal model will bind no detectable TNFα as compared with animals that express at least one of these TNFR proteins in wild-type form. The ability of cells from a subject animal model to bind TNFα may be assayed, for example, as described in Peschon et al. (1998) or by other suitable methods. For example, cells taken from a genetically modified animal may be tested for expression of functional TNFR I and II by being incubated with labeled biotinylated TNFα and streptavidin-conjugated phycoerythrin, then analyzed by flow cytometry to determine if the phycoerythrin was captured on the cells. Various cells may be isolated from the test animal to be used in such a binding assay, including conconavalin A-stimulated thymocytes, thioglycolate-elicited peritoneal exudate cells and bronchoalveolar lavage cells collected after intranasal administration of lipopolysaccharide (Peschon et al., 1998). If such cells from the mutated animal fail to bind labeled TNFα, this indicates that both types I and II TNFR are suitably inactivated.

In a preferred embodiment of the invention, the animal in which the p55 and p75 proteins are inactivated is a rodent strain that is susceptible to experimental collagen-induced arthritis (CIA). In a preferred embodiment, mutations are introduced into this rodent's genome that result in inactivation of the genes encoding the p55 and p75 TNFα receptors. In one preferred embodiment, the rodent is a strain of mouse or rat. Mice susceptible to CIA include mice that carry the $H-2^q$ MHC haplotype or the $H-2^r$ MHC haplotype. Exemplary strains of CIA-susceptible mice include the DBA/1, BUB and B10.Q strains, and exemplary strains of CIA-susceptible rats include the DA, BB-DR and LEW strains (see, for example, Joe and Wilder, Mol Med Today 5:367-369 (1999) and Anthony and Haqqi, Clin Exp Rheumatol 17:240-244 (1999)).

An exemplary animal model according to the invention is a DBA/1 mouse carrying double-null mutations in its p55 and p75 TNFR genes, that is, a $p55^{-/-}p75^{-/-}$ DBA/1 mouse. As used herein, a "null" mutation means that the gene is sufficiently changed relative to the wild-type gene such that it does not give rise to a protein that is recognizable by antibodies specific for the corresponding wild-type receptor protein. This may be accomplished by introducing a deletion or insertion into the wild-type gene, or by other means. Once established in a strain of mouse, a null mutation may be transferred to a different strain by appropriate genetic manipulations. A double-null mutation means that both alleles of that gene carry a null mutation.

In other embodiments, the genetic modifications may be introduced into rodent strains that are susceptible to forms of arthritis other than CIA, such as, for example, one of the arthritis-susceptible strains that are described in Joe and Wilder (1999).

Provided herein are methods that employ the subject animal model for screening assays to determine whether a candidate therapeutic agent is effective for treating autoimmune or chronic inflammatory conditions that are resistant to treatment with a TNFα inhibitor. TNFα inhibitors to which these diseases are unresponsive may include receptor-based TNFα inhibitors such as ENBREL® (Immunex Corporation) and LENERCEPT® (Roche) or other drugs that incorporate a soluble TNFR, humanized antibodies against TNFα such as REMICADE® (Centocor), D2E7 (BASF Pharma) or CDP571 (HUMICADE®; Celltech) or small molecules whose pharmacologic effectiveness may be based on reducing endogenous TNFα (such as, for example, pentoxifylline, thalidomide or others).

Candidate therapeutic agents that are tested in the subject assays are determined to be effective if when administered to the subject animal model the agent brings about a reduction in the severity of arthritis that has been induced in the animal. The severity of arthritis in the animal may be assessed by any desired method, which may be based, for example, on assigning to each animal a numerical score that reflects the degree of swelling or stiffness of the animal's limbs. Efficacy of a test agent in reducing the severity of disease is determined by comparing this score averaged over a group of arthritic animals that receive the test agent with the score for a group that receives a placebo. The test agent and placebo generally are administered over a period of at least one week, but may be administered for a longer period, for example, over a period of 2, 3, 4, 5, 6, 7 or 8 or more weeks. Alternatively, the effects of a single dose may be assessed using this model.

If DBA/1 $p55^{-/-}p75^{-/-}$ mice with CIA are used in the assays, an efficacious therapeutic agent will partially or fully ameliorate the symptoms of CIA in the mice. A reduction in severity of arthritis is determined to be present in DBA/1 $p55^{-/-}p75^{-/-}$ mice if the average clinical score (determined as described below) for an agent-treated group of mice is one or more clinical score units lower than the average clinical score for a group of negative control mice that are given a placebo. Preferably, the average clinical score in the agent-treated DBA/1 $p55^{-/-}p75^{-/-}$ mice will be at least 2 clinical score units lower than the placebo-treated mice, and more preferably it will be at least 5 units lower.

To determine clinical score for individual DBA/1 $p55^{-/-}p75^{-/-}$ mice in which CIA has been induced, the following index may be used in which each paw is assigned a score in clinical units based on the following:

0=normal appearance
1=erythema/edema in 1-2 digits
2=erythema/edema in >2 digits, or mild swelling in ankle/wrist joint
3=erythema/edema in entire paw
4=massive erythema/edema of entire paw extending into proximal joints;
ankylosis, loss of function Paw scores are combined for each mouse to determine a final score for that mouse, and then final scores for all animals in the test agent group are averaged and compared with the average score for the placebo-treated group. Generally, each test group will contain between 5 and 30 animals, though smaller or larger numbers of animals may be used. This or similar clinical scoring systems are suitable for evaluating CIA in DBA/1 $p55^{-/-}p75^{-/-}$ mice, but also are suitable for other species and for animal models involving types of experimental arthritis other than CIA. If desired, other kinds of arthritis scoring systems may be used, such as, for example, a system based on levels in the blood or other tissues of molecules that reflect the degree of inflammation or molecules that are specific disease markers.

When DBA/1 $p55^{-/-}p75^{-/-}$ mice are used, the CIA is induced according to the procedure given in Example 2, or using a similar protocol. In one preferred screening assay, a test agent is administered to a DBA/1 $p55^{-/-}p75^{-/-}$ mouse that is subjected to CIA induction, with the first dose of the agent being administered on the day the collagen boost is given, or the first dose may be delayed until the onset of symptoms, which generally take 15-60 days to appear in these mice. In this assay, negative control DBA/1 $p55^{-/-}p75^{-/-}$ mice are treated with a placebo, such as rat or mouse IgG or a physiologically acceptable saline solution. If desired, an agent known to be efficacious against CIA in these mice can be included in the assay as a positive control; for example, antibody against CD30L or against Il-1R1 can be used as a positive control (see Example 4), although this is optional. Doses of the test agent and control agent(s) may be administered daily, every two days, every three days, two times per week, one time per week, or less often if desired. The duration of the testing period is variable, and may continue, for example, for three days, one week, two weeks, three or for four or more weeks.

In the subject assays, the test agent and placebo may be administered by any suitable route, including orally administered liquid or solid forms, topical application, aerosol inhalation, transfection of host cells by recombinant DNA expressing the test agent, or by injection, including intraperitoneal, intravenous, subcutaneous or intramuscular injection. If desired, the test agent may be administered via a slow-release implant. When the test agent is incorporated into a slow-release formulation, very few doses are required, and a single dose may be used. If the test agent is an antibody and the subject is a mouse, the candidate therapeutic test agent may be administered at a dose of 20-75 µg/mouse, and is administered every day, every two to four days, or once a week. If the test agent is a small molecule, such as an organic molecule, suitable doses for testing are from 0.5-1000 µg/mouse, and the agent may be administered once every one to ten days. If a larger species of model animal is used, dose is adjusted upward in proportion to average body weight for the larger species.

Efficacy of the test agent in DBA/1 $p55^{-/-}p75^{-/-}$ mice or another strain of animal is determined by comparing the percentage of animals affected with arthritis in test and negative control groups, or by comparing the percentage of animals exhibiting severe disease during the testing period, and/or by comparing the mean clinical score for control groups and test groups after administration of the test agent. Mean clinical score may be determined according to the index described in Example 2, or by other suitable means. A test agent is determined to be useful for treating disorders resistant to TNFα inhibitors if animals to whom the test agent is administered exhibit a reduced severity of disease as compared with control animals that receive placebo instead of the test agent. In one preferred embodiment, the observed improvement is statistically significant, that is, $p<0.05$. Optionally, a dose dependency of the therapeutic response is established by administering the test agent at several different doses.

Candidate therapeutic agents to be screened in the subject animal model include any agent that is potentially effective for treating diseases that are resistant to treatment with TNFα inhibitors. This includes, for example, agents that target cytokines other than TNFα that are sometimes associated with inflammation (such as, for example, GM-CSF, interferon-γ, lymphotoxin-α, IL-1, IL-4, IL-8, IL-15, IL-17 and IL-18). Candidate therapeutic agents include soluble receptor molecules and antibodies specific for target cytokines or their receptors. Small organic molecules may also be screened using the subject animal model, including but not limited to agents with potential for interfering with CD30 or IL-1 signal transduction Therapeutic Methods Disclosed herein are methods for treating a variety of autoimmune and chronic inflammatory diseases by administering to a patient in need thereof an effective amount of one of the above-described agents. Blockers of CD30 signal transduction are used for treating any of the medical disorders listed below, and blockers of CD30 or IL-1 signal transduction are used for treating disorders listed below that respond poorly or not at all to treatment with a TNFα antagonist. In some instances, a disease is generally responsive to treatment with a TNFα inhibitor, but unresponsive in certain patients. An example of such a disease is rheumatoid arthritis. Rheumatoid arthritis patients who respond poorly or not at all to TNFα inhibitors will particularly benefit from treatment with an antagonist of the CD30/CD30L or IL-1/IL-R1 interaction.

Preferably, the patient is a human, and may be either a child or an adult. In one embodiment of the invention, a condition believed to be $T_H2$ driven or a condition characterized by high levels of expression of CD30 on activated T cells, is treated by administering a CD30 inhibitor concurrently with an IL-4 inhibitor.

For the subject therapeutic methods, the therapeutic agents preferably are administered in the form of a physiologically acceptable composition comprising a purified recombinant protein in conjunction with physiologically acceptable carriers, excipients and/or diluents. Such carriers are nontoxic to recipients at the dosages and concentrations employed. Compositions suitable for in vivo administration may be formulated according to methods well-known in the art. Components that are commonly employed in such formulations include those described in Remington's Pharmaceutical Sciences, 16th ed., 1980, Mack Publishing Company. Ordinarily, the preparation of such compositions entails combining the therapeutic agent with buffers, antioxidants such as ascorbic acid, low molecular weight polypeptides (such as those having fewer than 10 amino acids), proteins, amino acids, carbohydrates such as glucose, sucrose or dextrins, chelating agents such as EDTA, glutathione and other stabilizers and excipients. Neutral buffered saline or saline mixed with non-specific serum albumin are exemplary appropriate diluents. If desired, the therapeutic agent may be formulated as a lyophilizate using appropriate excipient solutions such as sucrose as a diluent. Appropriate dosages can be determined in standard dosing trials, and may vary according to the chosen route of administration. In accordance with appropriate industry standards, preservatives may also be added, such as benzyl alcohol.

The amount and frequency of administration may vary, depending on such factors as the nature and severity of the indication being treated, the desired response, the duration of treatment, the age, weight and condition of the patient, and so forth. The dose of a therapeutic agent may be adjusted to accommodate various routes of administration, or according to the needs of individual patients as determined by the patient's physician.

Arthritis may be treated by the methods and compositions disclosed herein. As used here, the term "arthritis" refers to chronic inflammatory conditions that primarily affect joints, or the connective tissue surrounding joints, although various body organs may also become affected. Arthritis may be autoimmune or traumatic in origin, or it may be triggered by exposure to a foreign antigen, thereafter leading to a chronic condition that is no longer dependent on the continued presence of the triggering antigen. The term "arthritis," as used herein, includes: arthritis deformans; osteoarthritis; rheumatoid arthritis (adult and juvenile); Lyme disease arthritis; reactive arthritis including Reiter's disease; psoriatic arthritis; arthritis nodosa; seronegative spondylarthropathies, including but not limited to ankylosing spondylitis. The efficacy of anti-CD30L treatment in treating arthritic disease is illustrated in Examples 2 and 4.

The subject inhibitors, compositions and combinations are useful in treating a variety of rheumatic disorders, which are defined herein as any chronic disorder involving painful and often multiple localized inflammations of the joints, muscles, nerves, tendons, skin, eyes, connective tissues or various other organ systems. These include but are not limited to: arthritis; scleroderma; gout; systemic lupus erythematosus; polymyalgia rheumatica; fibromyalgia; Still's disease; chronic uveitis; disorders resulting in inflammation of the voluntary muscle, including dermatomyositis and polymyositis, including sporadic inclusion body myositis; and inflammatory conditions such as chronic back or neck pain and sciatica. Systemic lupus erythematosus can cause inflammation of the joints, skin, kidneys, heart, lungs, blood vessels and brain. In its advanced forms, systemic lupus erythematosus this condition can result in kidney failure. Treatment with antibody against CD30L appeared to delay the progression of kidney failure in a mouse model for this disease (see Example 6).

Provided also are methods for using the subject inhibitors, compositions or combination therapies to treat various disorders of the endocrine system, including but not limited to: juvenile or maturity onset diabetes (including autoimmune, insulin-dependent types of diabetes; non-insulin dependent types and obesity-mediated diabetes); idiopathic adrenal atrophy; Addison's disease; hypothyroidism; Grave's disease; autoimmune thyroiditis, such as Hashimoto's thyroiditis; and polyglandular autoimmune syndromes (types I and II).

Conditions of the gastrointestinal system also are treatable with the subject inhibitors, compositions or combination therapies, including but not limited to: autoimmune sclerosing cholangitis; coeliac disease; inflammatory bowel diseases, including Crohn's disease and ulcerative colitis; autoimmune pancreatitis, including chronic pancreatitis; idiopathic gastroparesis; and idiopathic ulcers, including gastric and duodenal ulcers.

Included also are methods for using the subject inhibitors, compositions or combination therapies for treating disorders of the genitourinary system, such as autoimmune and idiopathic glomerulonephritis; and chronic idiopathic prostatitis (non-bacterial), including benign prostatic hypertrophy.

Also provided herein are methods for using the subject inhibitors, compositions or combination therapies to treat various hematologic disorders, including but not limited to: anemias and hematologic disorders, including pernicious anemia and aplastic anemia, and Fanconi's aplastic anemia; autoimmune hemolytic anemia; idiopathic thrombocytopenic purpura (ITP); myelodysplastic syndromes (including refractory anemia, refractory anemia with ringed sideroblasts, refractory anemia with excess blasts, refractory anemia with excess blasts in transformation); and autoimmune lymphoproliferative syndrome (ALPS).

In addition, the subject inhibitors, compositions and combination therapies are used to treat hereditary conditions such as Gaucher's disease, Huntington's disease, and muscular dystrophy.

The disclosed inhibitors, compositions and combination therapies are furthermore used to treat conditions that affect the liver such as autoimmune or chronic inflammatory hepatitis that is not due to viral infection.

In addition, the disclosed inhibitors, compositions and combination therapies are used to treat various autoimmune or chronic inflammatory disorders that involve hearing loss. One of these is inner ear or cochlear nerve-associated hearing loss that is thought to result from an autoimmune process, i.e., autoimmune hearing loss. This condition currently is treated with steroids, methotrexate and/or cyclophosphamide, which may be administered concurrently with an inhibitor of the CD30/CD30L interaction.

A number of inflammatory pulmonary disorders also can be treated with the disclosed inhibitors, compositions and combination therapies, including: idiopathic lymphangioleiomyomatosis; chronic obstructive pulmonary disease (COPD) associated with chronic non-infectious bronchitis or with emphysema; and fibrotic lung diseases, such as cystic fibrosis and idiopathic pulmonary fibrosis.

Disorders associated with transplantation also are treatable with the disclosed inhibitors, compositions or combination therapies, including graft-versus-host disease. To prevent or ameliorate graft-versus-host disease, the subject inhibitors may be administered prior to, concomitantly with, or following bone marrow or solid organ transplantation, including transplantation of heart, liver, lung, skin, kidney or other organs.

The subject inhibitors and the disclosed compositions and combination therapies also are useful for treating chronic inflammatory eye diseases, including autoimmune uveitis.

The subject inhibitors and the disclosed compositions and combination therapies also are useful for treating inflammatory disorders that affect the female reproductive system, including: multiple implant failure/infertility; fetal loss syndrome or IV embryo loss (spontaneous abortion); and endometriosis.

Other medical disorders treatable with the disclosed inhibitors, compositions and combination therapies include chronic degenerative diseases of the central nervous system. This includes, for example, diseases associated with demyelination, such as multiple sclerosis, systemic sclerosis and the Guillain-Barre syndromes (including acute inflammatory demyelinating polyneuropathy, acute motor axonal neuropathy, acute motor sensory axonal neuropathy and Fisher syndrome). In a preferred embodiment, multiple sclerosis is treated with an antagonist of the CD30/CD30L interaction (most preferably an antibody against CD30L) alone or concurrently with a TNFα inhibitor or an IL-4 inhibitor (most preferably sIL-4R). Multiple sclerosis is representative of a chronic, degenerative disease of the central nervous system, which besides the demyelinating conditions also include, for example, amyotrohpic lateral sclerosis (Lou Gehrig's Disease); Bell's palsy; Parkinson's disease and idiopathic chronic neuronal degeneration, all of which may be treated with an agent capable of inhibiting the interaction of CD30 and CD30. The efficacy of anti-CD30L antibody in ameliorating a multiple sclerosis-like disease is illustrated in Example 5.

Other chronic inflammatory conditions treatable with the disclosed inhibitors, compositions and combination therapies include cold agglutinin disease; Behcet's syndrome; Sjogren's syndrome; and idiopathic tenosynovitis, as well as various chronic inflammatory disorders associated with hereditary deficiencies. The subject inhibitors, compositions and combination therapies furthermore are useful for treating Bell's palsy (idiopathic facial paralysis); chronic fatigue syndrome (not associated with ongoing infection); chronic degenerative vertebral disc disease; Gulf war syndrome; and myasthenia gravis, which may be treated concurrently with corticosteroids.

Disorders involving the skin or mucous membranes also are treatable using the subject inhibitors, compositions or combination therapies. These include: acantholytic diseases, including Darier's disease, keratosis follicularis, pemphigus vulgaris and paraneoplastic pemphigus; acne rosacea; alopecia areata; bullous pemphigoid; eczema; erythema, including erythema multiforme and erythema multiforme bullosum (Stevens-Johnson syndrome); inflammatory skin disease; lichen planus; linear IgA bullous disease (chronic bullous dermatosis of childhood); loss of skin elasticity; neutrophilic dermatitis (Sweet's syndrome); pityriasis rubra pilaris; psoriasis; pyoderma gangrenosum; loss of skin elasticity; and toxic epidermal necrolysis.

Other diseases that can be treated with the disclosed compounds, compositions and combination therapies include: autoimmune-associated chronic mucocutaneous candidiasis; allergies; sarcoidosis; multicentric reticulohistiocytosis; Wegener's granulomatosis; arteritis, including giant cell arteritis; vasculitis and chronic autoimmune myocarditis.

To treat a medical disorder using the compounds and compositions provided herein, a therapeutically effective amount of a therapeutic agent according to the invention is administered to a mammal in need thereof. The agent is administered according to a regimen of dose and frequency of administration that is adequate to induce a sustained improvement in at least one indicator that reflects the severity of the disorder. An improvement is considered "sustained" if the patient exhibits the improvement on at least two occasions separated by at least one day, but preferably that are separated by one week, two weeks, three weeks or four or more weeks. The severity of the disorder is determined based on signs or symptoms, or may be determined by questionnaires that are administered to the patient, such as the quality-of-life questionnaires often used by physicians to assess the status of chronic disease conditions.

One or more indicators that reflect the severity of a patient's illness may be assessed for determining whether the frequency and duration of drug treatment is sufficient. The baseline value for a chosen indicator is established by examination of the patient prior to administration of the first dose of the therapeutic agent. Preferably, the baseline examination is done within about 60 days of administering the first dose.

For example, if the condition being treated is an arthritic condition, such as rheumatoid arthritis, psoriatic arthritis, osteoarthritis, one or more indicators for determining sufficiency of treatment may be chosen from among: number of tender, painful or swollen joints; degree of joint pain or tenderness or swelling; patient self-assessment (e.g., quality-of-life questionnaires), and physician assessment. For many arthritic diseases, the patient's self-assessment is a satisfactory indicator. Typical self-assessment questionnaires will reflect a patient's ability to conduct their daily activities, their perception of well-being, their level of pain and so on. The duration of treatment required to induce a measurable improvement for an arthritic or any other type of disease treatable as described herein is typically one to several weeks.

If the condition being treated is multiple sclerosis, suitable indicators for determining sufficiency of treatment include observing an improvement in one or more of the following: bladder and bowel control; fatigue; spasticity; body or hand tremors; muscle weakness; ability to walk; numbness in limbs; ability to concentrate (e.g., performance on a simple memory test); and subjective level of pain. Alternatively, the indicator may consist of the patient's score on a quality of life questionnaire as described above.

If the condition being treated is systemic lupus erythematosus, the indicator for determining sufficiency of treatment may consist of an observed improvement in one of the following: fatigue; fever; ulcers of the mouth and nose; facial rash ("butterfly rash"); photosensitivity (SLE often flares up after exposure to sunlight); pleuritis; pericarditis; Raynaud's phenomenon (reduced circulation to fingers and toes with exposure to cold); kidney function; and white blood cell count (SLE patients often have decreased numbers of white blood cells).

Improvement in a patient's condition is induced by repeatedly administering a dose of a therapeutic agent according to the invention until the patient manifests an improvement over baseline for the chosen indicator or indicators. In treating chronic conditions, a satisfactory degree of improvement usually is obtained after repeatedly administering the agent or agents over a period of at least a month or more, e.g., for one, two, or three months or longer. In some instances, improvement may occur sooner than one month, for example, after three weeks, two weeks, one week, or even after a single dose. A treatment duration of one to six weeks, or even a single dose, may be sufficient for treating occasional flare-ups in patients suffering from chronic conditions that tend to go into remission in-between flare-ups. For persistent conditions, treatment may be continued indefinitely if desired. Evan after a condition has shown improvement, maintenance therapy may be continued indefinitely at the same level or at a reduced dose or frequency of administration. If the dose or frequency of administration has been reduced, it may be resumed at the previous level if the patient's condition should worsen. In addition, treatment with inhibitors of the subject invention may be administered prophylactically to patients who are predisposed to an autoimmune or chronic inflammatory condition.

Any efficacious route of administration may be used to therapeutically administer the subject therapeutic agents, combinations and compositions. If injected, the agents can be administered, for example, via intra-articular, intravenous, intramuscular, intralesional, intraperitoneal or subcutaneous routes. Bolus injection or continuous infusion may be used. Other suitable means of administration include sustained release from microparticles, implants or the like, aerosol inhalation, eyedrops, oral preparations, including pills, syrups, lozenges or chewing gum, and topical preparations such as lotions, gels, sprays, ointments or other suitable techniques.

Alternatively, proteinaceous agents, such as antibodies or antigen-binding fragments thereof, may be administered by implanting cultured cells that express the protein. In one embodiment, the patient's own cells are induced to produce the therapeutic agent by transfection in vivo or ex vivo with a DNA that encodes a protein that blocks the CD30/CD30L, IL-1/IL-1R, IL-4/IL-4R or TNF/TNFR interactions. This DNA can be introduced into the patient's cells, for example, by using naked DNA or liposome-encapsulated DNA that encodes the agent, by using calcium-phosphate precipitated DNA, or by other means of transfection. Autologous cells that are transfected ex vivo are returned to the patient's body.

Regardless of the route of administration that is chosen, it is understood that the treatment regimens may be adjusted depending on the patient's needs, in accord with general principles of medicine.

When the therapeutic agent is an antibody, such as, for example, an antibody against CD30, CD30L, IL-1, IL-1R1, TNFα, IL-4 or IL-4R, preferred dose ranges for therapeutic or prophylactic purposes in humans include 0.1 to 20 mg/kg, or more preferably, 0.5-10 mg/kg. Another preferred dose range is 0.75 to 7.5 mg/kg, as exemplified in the experiments of Example 2 (adjusted for human body weight according to DeVita et al., eds., *Cancer—Principles & Practice of Oncology*, 4$^{th}$ Ed., J. B. Lippincott, 1993). A larger or smaller amount of antibody per dose may be used to accommodate differences in affinity of the antibody for the antigen. A suitable dose range for CD30:Fc is 0.01-20 mg/kg of body weight, or more preferably, 0.1-10 mg/kg of body weight. For other soluble proteins used as inhibitors in accord with the invention, suitable dose ranges include 2-500 μg/kg, 0.5-10 mg/kg and 10 to 50 mg/kg of body weight. It is understood that the skilled physician will adjust the dose and frequency of administration in accord with the needs of the patient and the nature of the disease being treated.

The following examples are offered by way of illustration, and not by way of limitation. Those skilled in the art will recognize that variations of the invention embodied in the examples can be made, especially in light of the teachings of the various references cited herein.

EXAMPLE 1

Monoclonal Antibodies Directed Against CD30L

A monoclonal antibody directed against murine CD30L was produced in rats as follows. Lewis rats were repeatedly immunized by the intraperitoneal route with 10-20×10$^6$ transfected CHO cells expressing full length murine CD30L. When serum titers were detected in the rats, they were given an intravenous boost with 10×10$^6$ transfected CHO cells. After three days, spleen cells from the immunized rats were fused with AG8.653 mouse myeloma cells. When hybridomas were well established in 96-well plates, supernatants from each well were screened by an ELISA assay that employed CHO cells that were transfected with DNA encoding CD30L (CELISA). For the CELISA, CHO cells expressing the recombinant CD30L were adhered to the ELISA plates, and each supernatant was screened for its ability to react with the CD30L expressed on the CHO cells. Hybridoma cells from positive wells were expanded in 48-well plates and screened by CELISA and also by fluorescence-activated cell sorting (FACS) using transfected and non-transfected CHO cells. Hybridoma cells that bound transfected but not non-transfected CHO cells were selected and screened further by FACS against mouse lymphoma cells that naturally express CD30L (EL4 cells). Hybridoma isolates that recognized both recombinant and naturally expressed CD30L were cloned twice by limiting dilution cloning, during which the activity of the supernatants was tracked at each step by CELISA and/or FACS assays. One of these clones, the M15 clone, was chosen for further propagation. In additional experiments, it was determined that the M15 antibody specifically blocked the binding interaction between murine CD30 and CD30L.

EXAMPLE 2

Treatment of Collagen-Induced Arthritis in Mice

Arthritis treatments that are effective in treating collagen-induced arthritis (CIA) are also effective in treating arthritis in humans (see, for example, Anthony and Haqqi, *Clin Exp Rheumatol* 17:240-244 (1999)), hence the effects of antagonizing the CD30/CD30L interaction was tested in CIA mice. Collagen-induced arthritis (CIA) was elicited in male DBA/1 mice (Harlan, UK) by injecting the mice with type II chicken collagen (Sigma). Mice were injected on day 0 with 100 μg of the collagen in complete Freund's adjuvant, and boosted on day 21 with a dose of 200 μg in incomplete Freund's adjuvant. Collagen injections were administered intradermally at the base of the tail. In this model, generally 75-100% of the mice are affected, that is, 75-100% of the mice exhibit arthritis symptoms after collagen injection. In these experiments, indicia of CIA usually appeared in affected mice by day 23.

Mice injected with collagen as described above were injected intraperitoneally with doses ranging from 0.15-150 µg of the M15 monoclonal antibody whose preparation is described in Example 1. Four experiments were conducted, each involving 13-15 mice per test group. In each of the four experiments, positive control mice received 150 µg of etanercept (ENBREL®, Immunex Corporation), which is known to be effective against CIA, and negative control mice received this same amount of human IgG (huIgG) or rat IgG. Daily injections of M15, etanercept or IgG were initiated on day 21, i.e., the day of the second collagen injection, and were continued until day 33.

During these experiments, mice were assessed three times per week for clinical signs of arthritis by an independent observer blinded to the treatment groups. Disease was evaluated using an arthritis index system that has been established for this model system. For scoring, each paw was assigned a clinical score based on the index. Paw scores were combined for each animal to determine a clinical score for that animal. The index used was as follows:

0=normal appearance
1=erythema/edema in 1-2 digits
2=erythema/edema in >2 digits, or mild swelling in ankle/wrist joint
3=erythema/edema in entire paw
4=massive erythema/edema of entire paw extending into proximal joints;
ankylosis, loss of function Improved mean clinical scores were evident in all groups that received M15 by the fifth day of M15 administration, and in one experiment by the third day of administration. Final results of the four experiments are summarized in Tables 1-4, shown below. Mean clinical scores, percent disease incidence (mice exhibiting CIA divided by total number of mice in group), and percent of affected mice exhibiting severe disease were calculated for each group of mice. Mice considered to have "severe disease" are those that had a clinical score greater than two at any time during the experiment. Statistical significance was determined for the differences in mean clinical score between the negative control group and the other groups of mice, based on scores on the last day of the experiment. Statistical significance was determined using a one-way analysis-of-variance (ANOVA) with Dunnett's method (H. J. Motuisky, *Analyzing Data with GraphPad Prism*, 1999, GraphPad Software, Inc., San Diego, Calif.). One-way ANOVA compares three or more groups when the data are categorized in one way. Dunnett's method compares control groups to treatment groups.

The first experiment tested the effects of administering to CIA mice a dose of 150 µg/day of the M15 antibody. By day 4 or 5 of this experiment, mean clinical score differences began to appear between negative control animals and those that received M15 or etanercept. The results of this first experiment are summarized in Table 1. As was expected, the mice that received etanercept (positive control group) exhibited a lower incidence of disease and a reduced incidence of severe disease when compared with the negative control mice that received HuIgG. The mice that received M15 also exhibited a lower disease incidence and a reduced percentage of mice with severe disease (see Table 1) as compared with negative controls. In addition, the M15 group had a lower mean clinical score than the negative controls on the last day of the experiment (day 33). For both the etanercept and the M15 groups, the last day differences in mean clinical score relative to negative controls were found to be statistically significant (p=0.05 or less).

TABLE 1

| Treatment | % Disease Incidence | Severe Disease | Mean Clinical Score on Last Day of Experiment |
|---|---|---|---|
| M15 | 53% | 27% | 2.53 |
| etanercept | 33% | 7% | 0.53 |
| HuIg | 87% | 80% | 6.47 |

A second experiment employed a similar protocol to compare doses of 50 µg and 150 µg of M15. The results are shown in Table 2. For this experiment, statistically significant improvement in mean clinical score was seen at the end of the experiment for both the etanercept group and for both doses of M15.

TABLE 2

| Treatment | % Disease Incidence | Severe Disease | Mean Clinical Score on Last Day of Experiment |
|---|---|---|---|
| M15, 150 µg | 40% | 20% | 1.2 |
| M15, 50 µg | 33% | 20% | 1.07 |
| etanercept | 47%% | 6% | 0.73 |
| HuIg | 87% | 80% | 7.53 |

In a third experiment, doses of 15, 50 and 150 µg of M15 were compared, and the results are summarized in Table 3. Again, mice that received M15 experienced a lower incidence of disease, as well as a lower incidence of severe disease as compared with negative controls. A statistically significant improvement in mean clinical score vis-a-vis controls was observed at all three doses of M15 in this experiment.

TABLE 3

| Treatment | % Disease Incidence | Severe Disease | Mean Clinical Score on Last Day |
|---|---|---|---|
| M15, 150 µg | 42% | 42% | 3.29 |
| M15, 50 µg | 71% | 57% | 3.71 |
| M15, 15 µg | 47% | 47% | 3.3 |
| etanercept | 53% | 20% | 1.33 |
| HuIg | 87% | 80% | 8.4 |

In a fourth experiment, 0.15, 1.5, 15 and 150 µg doses of M15 were tested, using rat IgG as the negative control. Results of this experiment are shown in Table 4. As seen in Table 4, improvement in mean clinical score exhibited a dose-dependency at the higher doses. For the 15 and 150 µg doses, the improvement in clinical score was statistically significant.

TABLE 4

| Treatment | % Disease Incidence | Severe Disease | Mean Clinical Score on Last Day |
|---|---|---|---|
| M15, 150 µg | 33% | 26% | 1.47 |
| M15, 15 µg | 80% | 33% | 2.67 |
| M15, 1.5 µg | 73% | 67% | 5.47 |
| M15, 0.15 µg | 67% | 67% | 5.67 |
| etanercept | 40% | 13% | 1 |
| rat IgG | 87% | 67% | 5.8 |

EXAMPLE 3

TNF-Independent Model of Murine Collagen-Induced Arthritis

A novel mouse was generated by moving previously described targeted null mutations in both the p55 and the p75 TNFα receptors (Peschon et al., *J Immunol* 160:943-952, 1998) from the CIA-insensitive C57BL/6 genetic background to the CIA-sensitive DBA/1 genetic background.

DBA/1 mice doubly deficient in p55 and p75 receptors (DBA/1 p55$^{-/-}$p75$^{-/-}$) were generated by crossing C57BL/6 p55$^{-/-}$-p75$^{-/-}$ mice (Peschon et al., 1998) with DBA/1 mice obtained from Jackson Laboratories. The resulting double heterozygotes were crossed again to DBA/1 mice. The resulting progeny that were heterozygous for both mutations were further tested for homozygosity at the DBA/1 MHC complex (required for CIA sensitivity) by FACS analysis using antibodies specific for C57BL/6 and DBA/1 MHC alleles. Antibodies against the C57BL/6 and DBA/1 MHC alleles were purchased from BD PharMingen.

Those progeny that were homozygous for the DBA/1 MHC were crossed to DBA/1 for another three generations to generate DBA/1 mice heterozygous for both p55 and p75 TNF receptor mutations (DBA/1 N5 p55$^{+/-}$-p$_{75}^{+/-}$; "N5" refers to the fifth backcross generation). DBA/1 N5 p55$^{+/-}$ p75$^{+/-}$ mice were intercrossed to establish a colony of DBA/1 mice doubly deficient in p55 and p75 TNF receptors (DBA/1 N5 p55$^{-/-}$p75$^{-/-}$). In order to identify mice that were homozygous for each of the null mutations, DNA from the progeny of the latter crosses was analyzed using PCR assays specific for the murine p55 and p75 TNFR genes, using DNA extracted from ear punches.

For tracking mutations in the p55 gene, the following PCR primers were used:

```
p60-B:
5'-GGATTGTCAC GGTGCCGTTG AAG-3'      (SEQ ID NO:9)

p60-E:
5'-CCGGTGGATG TGGAATGTGT G-3'        (SEQ ID NO:10)

p60-spe:
5'-TGCTGATGGG GATACATCCA TC-3'       (SEQ ID NO:11)

pgk5'-66:
5'-CCGGTGGATGTGGAATGTGTG-3'          (SEQ ID NO:12)
```

Twenty-five pmole each of the four primers listed above were added to the ear punch DNA and the mixture subjected to 32 cycles of PCR for 1 minute at 94°, 1 min. 65° and 30 seconds at 72°. PCR products were resolved and visualized on 3% USB fine resolution agarose (cat. # 73422) gels run in TAE buffer and stained in ethidium bromide. Expected PCR products using the above primers were 120 bp for p55$^{+/+}$, and 155 bp for p55$^{-/-}$. Heterozygous mice were expected to yield both products. Additional nonspecific products migrating at about 300-500 bp were seen occasionally in p55$^{-/-}$ mice.

The following primers were used to track the p75 mutations:

```
p80-Kas:
5'-AGAGCTCCAGGCACAAGGGC-3'           (SEQ ID NO:13)

p80i-1:
5'-AACGGGCCAGACCTCGGGT-3'            (SEQ ID NO:14)

pgk5'-66:
5'-CCGGTGGATGTGGAATGTGTG-3'          (SEQ ID NO:12)
```

These PCR reactions used 50 pmole p80-Kas, 100 pmole p80i-1 and 20 pmole pgk5'-66 for 32-34 cycles for 1 minute at 94°, 1 minute at 65° and 30 seconds at 72°. PCR products were resolved and visualized on 3% USB fine resolution agarose gels run in TAE buffer and stained in ethidium bromide. p75$^{+/+}$ mice were expected to yield a 275 bp product, and p75$^{-/-}$ mice to yield a 160 bp product. Heterozygotes were expected to yield both products. Additional nonspecific products were occasionally seen migrating at about 50-100 bp.

Homozygous DBA/1 p55$^{-/-}$p75$^{-/-}$ mice were thus identified using PCR and thereafter were interbred.

EXAMPLE 4

Collagen-Induced Arthritis in DBA/1 p55$^{-/-}$p75$^{-/-}$ Mice

The following experiments using the p55$^{-/-}$p75$^{-/-}$ DBA/1 mice of Example 3 demonstrate that TNFα-independent CIA can be effectively treated either by administering a test agent that inhibits signal transduction by CD30 or IL-1.

CIA was induced in p55$^{-/-}$p75$^{-/-}$ DBA/1 mice by administering heterologous type II collagen according to the protocol described above in Example 2. Two experiments were conducted, each using 15 mice per test group. These experiments were designed to determine whether the inhibitors being tested could prevent the development of CIA in these mice. Mice were randomly divided into groups (n=15) at the time of the boost and were injected daily with either the test agent or the control protein for 14 days.

Compared with wild-type DBA/1 mice, the DBA/1 p55$^{-/-}$ p75$^{-/-}$ mice injected with collagen displayed a delayed onset and slower course of disease. However, significant clinical symptoms appeared in the mutant mice 15-60 days after the second collagen injection. As expected, no diminution of arthritis symptoms was observed in DBA/1 p55$^{-/-}$p75$^{-/-}$ mice when they were treated with p75 TNFR.Fc (ENBREL®; Immunex Corporation). In contrast, ENBREL® is highly effective in reducing arthritis symptoms in wild-type DBA/1 mice with CIA (see Example 2 above). Thus, the arthritis observed in the p55$^{-/-}$p75$^{-/-}$ DBA/1 mice is not mediated by TNFα.

Experiments were conducted to determine whether molecules other than TNFα played a role in CIA in DBA/1 p55$^{-/-}$p75$^{-/-}$ mice. In these experiments, agents that inhibit the CD30/CD30L or the IL-1/IL-1R1 interaction were tested to see if they would affect CIA in this animal model. Monoclonal antibodies against either IL-1R1 (M147; Immunex Corporation) or murine CD30L (M15; preparation described in Example 1) were administered by intraperitoneal injection to these mice, while control mice received rat IgG. Each experimental group consisted of 15 mice. Antibody treatment was initiated at day 21 (at the time of the collagen boost), and was administered for 21 days for experiment #1, and for 28 days in experiment #2. For M15 antibody, a dose of 50 µg was administered per day, and for the M147 antibody, a dose of 50 µg was administered every two days. Clinical score was determined three times per week, using the clinical scoring system described in Example 2.

As illustrated in Table 5 (experiment #1) and Table 6 (experiment #2), the administration of M147 or M15 significantly reduced arthritis in the DBA/1 p55$^{-/-}$p75$^{-/-}$ mice, with M147 resulting in an almost complete amelioration of disease.

TABLE 5

| Treatment | % Disease Incidence | Severe Disease | Mean Clinical Score on Last Day |
|---|---|---|---|
| M15 | 26% | 0.06% | 0.75 |
| M147 | 0.06% | 0% | 0.07 |
| rat IgG | 67% | 60% | 4.27 |

TABLE 6

| Treatment | % Disease Incidence | Severe Disease | Mean Clinical Score on Last Day |
|---|---|---|---|
| M15 | 60% | 40% | 2.7 |
| M147 | 0% | 0% | 0 |
| rat IgG | 80% | 67% | 4.1 |

The results of these two experiments show that collagen-induced arthritis can be established in a TNFα-independent manner, and that inhibiting either the IL-1/IL-1R1 or CD30/CD30L interactions effectively reduce disease in these mice.

EXAMPLE 5

Mouse Experimental Allergic Encephalomyelitis Model

This example demonstrates the efficacy of antagonists of the CD30/CD30L interaction for treating multiple sclerosis. A mouse model for multiple sclerosis was employed for this purpose. Chronic experimental autoimmune encephalomyelitis (EAE), which is a well accepted experimental model for this disease, was induced in female C57BL/6 mice (Taconic Farms Inc., Germantown, N.Y.) using a modification of the protocol described by Mendel et al. (*Eur. J Immunol.* 25:1951-59, 1995). In brief, disease induction involved the immunization of mice with the MOG35-55 peptide derived from rat myelin oligodendrocyte glycoprotein (Mendel et al., 1995). Modifications to the disease induction protocol of Mendel et al. included the use of a lower dose of MOG35-55 for immunization (see below), no booster immunization, and the use of RIBI® adjuvant instead of complete Freund's adjuvant.

To induce EAE, groups of age and weight-matched mice (11-13 mice per group) were given a dose of 100 µg of rat MOG35-55. The MOG35-55 was emulsified in 0.2 ml RIBI adjuvant (Corixa Corporation), and injected subcutaneously at three sites distributed over the shaved flank. To induce EAE with accelerated onset, the mice in a second experiment (Experiment 2) received by intravenous injection 500 ng pertussis toxin (List Biological Laboratory Inc, Campbell, Calif.), which was administered 48 hours after they received their dose of MOG35-55. The mice in Experiment 1 received no pertussis toxin, thus disease onset in Experiment 2 was accelerated as compared with Experiment 1.

Administration of antibody or placebo was initiated on the day after the MOG35-55 was administered (day 1) and was continued through day 11. Each mouse was injected intraperitoneally every other day with 0.2 ml pyrogen-free phosphate-buffered saline (PBS) or 0.2 ml PBS containing one of the following: (i) 100 µg M15 (anti-CD30L); (ii) 100 µg rat IgG (Sigma); or (iii) 75 µg M147 (anti-IL1R1). Endotoxin levels were <10 EU/mg of protein for all reagents. Mice were monitored daily for 35 days (Experiment 1) or 30 days (Experiment 2) for weight loss, disease onset and severity of clinical signs of EAE by an independent observer blinded to the treatment groups.

The severity of EAE was assessed using a standard EAE index system in which "0" is used to indicate an asymptomatic mouse and clinical scores ranging from 0.5 to 4 was used to indicate varying degrees of ascending paralysis. The severity of EAE was assessed using a slightly modified version of a commonly used EAE scoring system. In this system, "0" were used to indicate a mouse with no evidence of disease and scores of 1-5 were used to indicate varying degrees of ascending paralysis as follows: 1, tail paralysis; 2, hind limb weakness; 3, partial hind limb paralysis; 4, complete hind limb paralysis; 5, moribund or dead. The disease protocol described above induces an acute episode of disease in control mice (peak score of 2-4) from which most recover at least partially. Thus the acute episode of disease is not lethal and mice do not reach a score of 5. The aforedescribed scale was modified to include a score of "0.5" which was given to mice that showed the earliest signs of EAE but that did not exhibit complete paralysis of the tail. Mice given a score of 0.5 exhibited some or all of the following symptoms: overnight weight loss of 1-2 grams; noticeable tremor when held up by the tail; and weakness at the distal tip of the tail.

The median day of onset of EAE was determined by Kaplan-Meier Survival analysis. Significant differences in onset between groups were assessed using a Log-Rank comparison. Fischer's exact test was used to analyze the statistical significance of differences in the incidence of EAE among the groups of mice.

Results of these two experiments demonstrated the ameliorating effects of either of the tested antibodies on the onset, incidence and severity of the clinical course of EAE. As shown below in Table 7, administration of either anti-CD30L (M15) or anti-IL-1R1 (M147) resulted in delayed disease onset and a reduced incidence of disease in both of the experiments.

TABLE 7

| Group | Incidence (%) | | Combined Results | Median Day of Onset | |
| | Expt 1 | Expt 2 | | Expt 1 | Expt 2 |
|---|---|---|---|---|---|
| PBS | 10/11 (91%) | 11/13 (85%) | 21/24 (88%) | 22 | 16 |
| rat IgG | 9/11 (82%) | 12/13 (92%) | 21/24 (88%) | 21 | 16 |
| anti-CD30L | 6/11 (55%) | 8/13 (62%) | 14/24 (58%) | 35 | 23 |
| anti-IL-1R | 5/11 (45%) | 9/13 (69%) | 14/24 (58%) | not determined | 25 |

In Table 7, for the combined results for mice that received M15 or M147, when compared with the rat IgG group, p<0.05 for the incidence of disease. In Experiment 1, for median day of onset for the M15 mice, p=0.067 vs Rat IgG and p<0.05 vs PBS. In Experiment 2 in Table 5, for median day of onset, p<0.005 vs rat IgG for both the M15 and M147 groups.

For these same two experiments, Table 8 shows the mean percent change in body weights within each group over the acute course of disease. As shown in Table 8, mice that received either anti-CD30L or anti-IL-1R1 antibodies lost less weight during this time than mice that received rat IgG or PBS.

TABLE 8

| | Treatment | Mean Percent Body Weight Change ± SEM (All mice) | Mean Percent Body Weight Change ± SEM (Affected mice only) |
|---|---|---|---|
| Expt 1 | anti-CD30L | −2.0 ± 2.4* | −6.2 ± 2.7 |
| | anti-IL-1RI | −1.5 ± 1.9** | −5.4 ± 3.2 |
| | PBS | −7.3 ± 3.1 | −9.2 ± 2.7 |
| | Rat IgG | −9.7 ± 1.8 | −11.4 ± 1.75 |
| Expt 2 | anti-CD30L | 0.7 ± 2.1*** | −5.3 ± 2.0** |
| | anti-IL-1RI | −7.7 ± 3.5* | −13.3 ± 3.7 |
| | PBS | −16.3 ± 2.9 | −19.9 ± 1.8 |
| | Rat IgG | −19.9 ± 2.9 | −21.7 ± 2.6 |

To calculate the weight data in Table 8, the baseline weight for each mouse was defined as its weight on day 12 (Experiment 1) or day 10 (Experiment 2) relative to immunization. These days were chosen as reference points because all of the mice in each experiment were weight-matched on day 0 and the mean weight of all the groups increased in a similar manner between days 0-12 (Experiment 1) or days 0-10 (Experiment 2). The mean weights of the various groups diverged after these time points due to weight loss associated with the onset of EAE. The left-hand column of Table 8 shows the mean percent body weight change calculated for all of the mice in each treatment group, that is, both the clinically affected (clinical score of at least 0.5) and non-affected mice were included for this calculation. The right-hand column of Table 8 shows the mean body weight change during the acute phase of the disease for only the mice that were clinically affected. Body weight change for the affected mice was calculated based on the difference between the baseline weight of each individual mouse and the minimum weight observed for that mouse after the onset of disease. For those mice that never showed clinical evidence of disease, the percent body weight change for Table 8 was calculated by comparing the baseline weight of each non-affected mouse to its weight on day 25 of the experiment.

The data in Table 8 illustrate that either anti-CD30L or anti-IL-R1 is effective in slowing the weight loss otherwise observed in mice injected with MOG35-55. The Student's t test was used to determine the statistical significance of these body weight differences. Numbers found to be statistically significant are marked with asterisks in Table 8, and p values were as follows: *$p<0.05$ vs rat IgG controls; $p<0.01$ vs rat IgG controls; *$p<0.001$ vs rat IgG controls.

Table 9 presents the clinical score results for Experiments 1 and 2. Group means and SEM were calculated based on the peak clinical score for each mouse (0 for non-affected mice; 0.5 to 4 for affected mice). The mean peak clinical score for each antibody-treated group was compared with the rat IgG-treated group using the Student's t test, and the p values are shown in the last column of Table 9.

TABLE 9

| | Treatment | Mean Peak Clinical Score (±SEM (scale 0–4)) | p vs Rat IgG |
|---|---|---|---|
| Expt 1 | anti-CD30L | 1.1 ± 0.3 | 0.0621 |
| | anti-IL-1RI | 0.9 ± 0.3* | 0.0362 |
| | PBS | 2.0 ± 0.3 | 0.7402 |
| | Rat IgG | 2.1 ± 0.4 | NA |

TABLE 9-continued

| | Treatment | Mean Peak Clinical Score (±SEM (scale 0–4)) | p vs Rat IgG |
|---|---|---|---|
| Expt 2 | anti-CD30L | 1.3 ± 0.4* | 0.0122 |
| | anti-IL-1RI | 1.3 ± 0.3* | 0.0056 |
| | PBS | 2.2 ± 0.3 | 0.3262 |
| | Rat IgG | 2.7 ± 0.3 | NA |

As shown in Table 9, significant differences in clinical score were observed between groups of mice treated with either M15 or M147, as compared with the control mice. Differences that were determined to be statistically significant ($p<0.05$) are marked in Table 9 with an asterisk.

EXAMPLE 6

Blocking CD30L Delays Kidney Failure in a Murine Model of Systemic Lupus Erythematosus Female (NZB×NZW)$_{F1}$ hybrid mice (referred to hereafter as "NZB/W mice") spontaneously develop a lupus-like disease characterized by the presence of serum autoantibodies to double-stranded DNA (dsDNA). These mice, which eventually experience total kidney failure, are often used as a model for experimentation directed at better understanding and treating lupus in humans. Over time, this condition in NZB/W mice progresses to kidney malfunction as manifested by the appearance of proteinuria. In a trial experiment to study the onset and progression of disease in these mice, about half had serum anti-dsDNA titers and about 10% had proteinurea by 26 weeks of age. By 38 weeks of age, 20% of the mice had died, and of the remaining mice, 52% were proteinurea positive and 98% had serum anti-dsDNA titers.

Female NZB/W mice 32 weeks of age were used in an experiment to determine whether anti-CD30L could delay the development of lupus-like disease. Within a group of 32 week old mice, 98% were serum positive for antibodies against dsDNA (detected by ELISA), but only 40% had progressed to renal disease as assessed by proteinuria (detected using CHEMSTRIP®; Roche). Mice from this group that were negative for proteinuria were used in the following experiment.

Thirty-two week old NZ/B mice that did not have proteinuria were divided into two groups, and each group was treated every other day with 150 μg of either anti-CD30L (M15) (group of 10 mice) or rat IgG as a control (group of 9 mice), administered by intraperitoneal injection. Treatments were continued for five weeks, and the mice were assessed weekly for the presence of proteinuria. Approximate values for the percentages calculated from the results of this experiment are summarized in Table 10 below.

TABLE 10

| | Percent Incidence Progression to Proteinuria | | | | |
|---|---|---|---|---|---|
| Treatment | Week 1 | Week 2 | Week 3 | Week 4 | Week 5 |
| Anti-CD30L | 10% | 10% | 10% | 10% | 20% |
| Rat IgG | 0% | 10% | 20% | 30% | 40% |

The data in Table 10 shows a trend toward decreased incidence of proteinuria in mice treated with anti-CD30L as compared with control mice. A scale from 1-5 was used to assess the degree of proteinurea among these mice. At five weeks, the mean proteinurea index for control mice in this experiment was 1.7, whereas M15-treated mice had a mean proteinurea index of 0.6. This result suggests that humans suffering from systemic lupus erythematosus might benefit from treatment with antibodies against CD30L or with other antagonists of the CD30/CD30L interaction.

To confirm the result presented above, a second group of female NZB/W mice are randomly assigned to treatment groups as antibodies against dsDNA first appear in their serum. This experiment is designed to test the effects of treatment on the progression of anti-dsDNA titers and the progression of proteinurea. One group of mice is treated with 150 µg of anti-CD30L (M15), and the other group is treated with rat IgG as a control. Treatments are administered three times per week by intraperitoneal injection for a period of three weeks. Mice are monitored weekly for titers of serum antibodies to dsDNA and for the appearance of proteinuria.

In other experiments, the efficacy of anti-CD30L treatment will be tested in a model of chemically induced lupus. In this model, administration of the isoprenoid alkane pristane (2,6,10,14 tetramethylpentadecane) induces autoantibody production and immune complex mediated glomerulonephritis. One advantage of this model is that it is not restricted to a particular mouse strain. Initial experiments are underway in normal BALB/c and C57BL/6 strains of mice.

What is claimed is:

1. A method of treating psoriatic arthritis; arthritis nodosa; seronegative spondylarthropathy, and ulcerative colitis in a patient, said method comprising administering to the patient an antibody specific for CD30L that is capable of inhibiting the binding of CD30 to CD30L concurrently with an antagonist of IL-1α, wherein the antibody is administered according to a regimen of dose and frequency of administration that is adequate to induce a sustained improvement in at least one indicator that reflects the severity of the patient's condition, the improvement being considered sustained if the patient exhibits the improvement on at least two occasions separated by at least one day.

2. The method according to claim 1, wherein the patient is a human.

3. The method according to claim 2, wherein the seronegative spondylarthropathy is ankylosing spondylitis.

4. The method according to claim 2, wherein the psoriatic arthritis is treated.

5. The method according to claim 2, wherein the antibody specific for CD30L is a monoclonal antibody.

6. The method according to claim 5, wherein to antibody specific for CD30L is a humanized antibody.

7. The method according to claim 5, wherein the antibody specific for CD30L is a human antibody.

8. The method according to claim 3, wherein the antibody specific for CD30L is a monoclonal antibody.

9. The method according to claim 8, wherein the antibody specific for CD30L is a humanized antibody.

10. The method according to claim 8, wherein the antibody specific for CD30L is a human antibody.

11. The method according to claim 4, wherein the antibody specific for CD30L is a monoclonal antibody.

12. The method according to claim 11, wherein the antibody specific for CD30L is a humanized antibody.

13. The method according to claim 11, wherein the antibody specific for CD30L is a human antibody.

* * * * *